(12) United States Patent
Epstein et al.

(10) Patent No.: US 8,795,672 B2
(45) Date of Patent: Aug. 5, 2014

(54) COMPOSITIONS AND METHODS FOR CANCER IMMUNOTHERAPY

(75) Inventors: Alan L. Epstein, La Canada, CA (US); Jiali Li, Monterey Park, CA (US); Peisheng Hu, Covina, CA (US)

(73) Assignee: University of Southern California, Los Angeles, CA (US)

( * ) Notice: Subject to any disclaimer, the term of this patent is extended or adjusted under 35 U.S.C. 154(b) by 892 days.

(21) Appl. No.: 10/779,267

(22) Filed: Feb. 13, 2004

(65) Prior Publication Data
US 2004/0228836 A1 Nov. 18, 2004

Related U.S. Application Data

(60) Provisional application No. 60/447,714, filed on Feb. 14, 2003.

(51) Int. Cl.
*A61K 39/395* (2006.01)

(52) U.S. Cl.
USPC ............... 424/178.1; 530/387.1; 424/198.1

(58) Field of Classification Search
USPC ............... 435/7.23, 7.1, 287.2, 69.7; 436/547
See application file for complete search history.

(56) References Cited

U.S. PATENT DOCUMENTS

| | | | |
|---|---|---|---|
| 4,816,567 A | 3/1989 | Cabilly et al. | |
| 4,956,778 A | 9/1990 | Naito | |
| 5,091,513 A | 2/1992 | Huston et al. | |
| 5,116,943 A | 5/1992 | Koths et al. | |
| 5,132,405 A | 7/1992 | Huston et al. | |
| 5,565,332 A | 10/1996 | Hoogenboom et al. | |
| 5,767,071 A | 6/1998 | Palladino et al. | |
| 5,780,426 A | 7/1998 | Palladino et al. | |
| 5,824,782 A * | 10/1998 | Holzer et al. | 530/391.1 |
| 6,013,625 A | 1/2000 | Pierschbacher et al. | |
| 6,331,415 B1 | 12/2001 | Cabilly et al. | |
| 6,365,619 B1 | 4/2002 | Shi | |
| 8,545,838 B2 | 10/2013 | Epstein et al. | |
| 2003/0138413 A1 | 7/2003 | Vicari et al. | |
| 2003/0148982 A1 | 8/2003 | Brenner et al. | |
| 2004/0077835 A1* | 4/2004 | Offord et al. | 530/351 |

FOREIGN PATENT DOCUMENTS

| | | |
|---|---|---|
| JP | 2002-519065 | 7/2002 |
| WO | WO-00/01822 | 1/2000 |

OTHER PUBLICATIONS

Giovarelli M, Cappello P, Forni G, et al., Tumor rejection and immune memory elicited by locally released LEC chemokine are associated with an impressive rerecruitment of APCs, lymphocytes, and granulocytes. J Immunol. Mar. 15, 2000;164 (6): 3200-6.*
Hornick JL, Sharif J, Khawli LA, Hu P, Biela BH, et al., A new chemically modified chimeric TNT-3 monoclonal antibody directed against DNA for the radioimmunotherapy of solid tumors. Cancer Biother Radiopharm. Aug. 1998;13(4):255-68.*
Clark Protein Engineering of Antibody Molecules for Prophylactic and Therapeutic Applications in Man, 1993, p. 1.*
Honick et al., Clin Cancer Research, vol. 5, p. 51-60, 1999.*
Sequence search result.*
Altschul et al., "Gapped Blast and PSI-Blast: a New Generation of Protein Database Search Programs," *Nucl. Acids Res.* 25:3389-3402 (1997).
Altschul et al., "Basic Local Alignment Search Tool," *J. Mol. Biol.* 215:403-410 (1990).
Arap et al., "The Human Vascular Mapping Project. Selection and Utilization of Molecules for Tumor Endothelial Targeting," *Haemostasis* 31 (Suppl 1): 30-31 (2001).
Chang et al., "The Discovery of Small Molecule Carbamates as Potent Dual $x_4\beta_1/x_4\beta_7$ Integrin Antagonists," *Bioorganic & Medicinal Chem Letters* 12:159-163 (2002).
Chen et al., "Diffusion and Binding of Monoclonal Antibody TNT-1 in Multicellular Tumor Spheroids," *J. Natl. Cancer Inst.* 83:200-204 (1991).
Chen et al., "A Comparative Autoradiographic Study Demonstrating Differential IntraTumor Localization of Monoclonal Antibodies to Cell Surface (Lym-1) and Intracellular (TNT-1) Antigens," *J. Nucl. Med.* 31:1059-1066 (1990).
Dela Cruz, et al., "Recombinant Anti-Human HER2/*neu* IgG3-(GM-CSF) Fusion Protein Retains Antigen Specificity and Cytokine Function and Demonstrates Antitumor Activity," *J.Immuno.* 165: 5112-5121 (2000).
Epstein et al., "Radioimmunodetection of Necrotic Lesions in Human Tumors Using I-131 Labeled TNT-1 F(ab')$_2$ Monoclonal Antibody," *Antibody, Immunoconj, & Radiopharm* 4:151-161 (1991).
Epstein et al., "A Novel Method for the Detection of Necrotic Lesions in Human Cancers," *Cancer Res* 48:5842-5848 (1988).
Francis et al., "PEGylation of Cytokines and Other Therapeutic Proteins and Peptides: The Importance of Biological Optimisation of Coupling Techniques," *Int J. Hematol.* 68:1-18 (1998).
Gerard, et al., "Chemokines and Disease," *Nature Immunol.* 2:108-115 (2001).
Giovarelli et al., Tumor Rejection and Immune Memory Elicited by Locally Released LEC Chemokine are Associated with an Impressive Recruitment of APCs, Lymphocytes, and Granulocytes. *J Immunol.* 164:3200-3206 (2000).
Hedrick et al., "Characterization of a Novel CC Chemokine, HCC-4, Whose Expression is Increased by Interleukin-10," *Blood* 91:4242-4247 (1998).

(Continued)

*Primary Examiner* — Lei Yao
(74) *Attorney, Agent, or Firm* — Foley & Lardner LLP; Antoinette F. Konski

(57) ABSTRACT

Provided is a cancer therapeutic agent comprising a cancer targeting molecule linked to a liver-expressed chemokine (LEC). In one embodiment, the cancer targeting molecule is an antibody that targets cancer cells or tumors in vivo. The cancer targeting molecule is associated non-covalently or covalently with LEC. The cancer therapeutic agents of the invention are useful for the treatment of cancer in an individual by reducing the size of a tumor or inhibiting the growth of cancer cells in an individual and/or by inhibiting the development of metastasis. The effectiveness of the therapy using the LEC cancer therapeutic agents can be increased by reducing the activity of immunoregulatory T cells and/or by adoptively transferring immune T cells.

7 Claims, 9 Drawing Sheets

(56) References Cited

OTHER PUBLICATIONS

Henikoff and Henikoff, "Amino Acid Substitution Matrices From Protein Blocks," *Proc. Natl. Acad. Sci. USA* 89:10915-10919 (1992).

Hogan, et al. "Measurement of Tumor Necrosis Factor α and β," *Current Protocols in Immunology* 37:6.10.1-6.10.5 (2000).

Hornick et al. "A New Chemically Modified Chimeric TNT-3 Monoclonal Antibody Directed Against DNA for the Radioimmunotherapy of Solid Tumors," *Cancer Biother and Radiopharm* 13:255-268 (1998).

Hornick et al., "Pretreatment With a Monoclonal Antibody/Interleukin-2 Fusion Protein Directed Against DNA Enhances the Delivery of Therapeutic Molecules to Solid Tumors," *Clin Cancer Res*, 5:51-60 (1999).

Hornick et al., "Chimeric CLL-1 Antibody Fusion Proteins Containing Granulocyte-Macrophage Colony-Stimulating Factor or Interleukin-2 With Specificity for B-Cell Malignancies Exhibit Enhanced Effector Functions While Retaining Tumor Targeting Properties," *Blood*, 89:4437-4447 (1997).

Howard et al., "LEC Induces Chemotaxis and Adhesion by Interacting with CCR1 and CCR8," *Blood* 96:840-845 (2000).

Huston et al., "Protein Engineering of Antibody Binding Sites: Recovery of Specific Activity in an Anti-Digoxin Single-Chain Fv Analogue Produced in *Escherichia coli*," *Proc. Nat. Acad. Sci. USA* 85:5879-5883 (1988).

June, C.H., "Can't Get Any Help? New Approaches for Adoptive Immunotherapy of Cancer," *J. Immunother* 24(5):389-391 (2001).

Katre, N.V., "Immunogenicity of Recombinant Il-2 Modified by Covalent Attachment of Polyethylene Glycol," *J. Immunol.* 144:209-213 (1990).

Khawli et al., "Pharmacokinetic Characteristics and Biodistribution of Radioiodinated Chimeric TNT-1, -2, and -3 Monoclonal Antibodies After Chemical Modification with Biotin," *Cancer Biotherapy & Radiopharmaceuticals* 17: 359-370 (2002).

Khawli et al., "Effect of Seven New Vasoactive Immunoconjugates on the Enhancement of Monoclonal Antibody Uptake in Tumors," *Cancer* 73:824-831 (1994).

Kim et al., "A Nitric Oxide Production Bioassay for Interferon-γ," *Journal of Immunological Methods* 198:203-209 (1996).

Leberthon et al., "Enhanced Tumor Uptake of Macromolecules Induced by a Novel Vasoactive Interleukin 2 Immunoconjugate," *Cancer Res.*, 51:2694-2698 (1991).

Li et al., "Complete regression of experimental solid tumors by combination LEC/chTNT-3 immunotherapy and CD25+ T-cell division." Cancer Research, 63:8384-8392, 2003.

Li et al., "LEC/chTNT-3 fusion protein for the immunotherapy of experimental solid tumors." Journal of Immunotherapy, 26(4): 320-331, 2003.

Lin et al., "Specific and Dual Antagonists of $x_4\beta_1$ and $x_4\beta_7$ Integrins," *Bioorganic & Medicinal Chem Lett*, 12:133-136 (2002).

Lum, et al., "Immune Modulation in Cancer Patients After Adoptive Transfer of Anti-CD3/Anti-CD28-Costimulated T Cells—Phase 1 Clinical Trial," *Journal of Immunology* 24:408-419 (2001).

Mackay, C.R., "Chemokines: Immunology's High Impact Factors," *Nature Immunol.* 2:95-101 (2001).

Meiser et al., "Chimeric Monoclonal CD4 Antibody—A Novel Immunosuppressant for Clinical Heart Transplantation," *Transplantation* 58(4):419-423 (1994).

Miller et al., "Immunologic and Biochemical Analysis of TNT-1 and TNT-2 Monoclonal Antibody Binding to Histones," *Hybridoma* 12:689-698 (1993).

Mitchison, N.A., "Studies on the Immunological Response to Foreign Tumor Transplants in the Mouse," *J Exp Med*. 102:157-177 (1955).

Miyagishi, et al., "Macrophage Inflammatory Protein-1α in the Cerebrospinal Fluid of Patients with Multiple Sclerosis and Other Inflammatory Neurological Diseases, "*J Neuro Sci*. 129:223-227 (1995).

Mizokami et al., "Chimeric TNT-3 Antibody Murine Interferon-γ Fusion Protein for the Immunotherapy of Solid Malignancies," *Hybridoma and Hybridomics* 22:197-207 (2003).

Moser, et al., "Lymphocyte Traffic Control by Chemokines," *Nature Immunology* 2:123-128 (2001).

Naruse, et al., "A YAC Contig of the Human CC Chemokine Genes Clustered on Chromosome 17q11.2," *Genomics* 34:236-240 (1996).

Needleman and Wunsch, "A General Method Applicable to the Search for Similarities in the Amino Acid Sequence of Two Proteins," *J. Mol. Biol.* 48:443-453 (1970).

Nomiyama et al., "Human CC Chemokine Liver-Expressed Chemokine/CCL16 is a Functional Ligand for CCR1, CCR2 and CCR5, and Constitutively Expressed by Hepatocytes," *Int Immunol.* 13(8):1021-1029 (2001).

Oppenheim, et al., "Introduction to the Role of Cytokines in Innate Host Defense and Adaptive Immunity" In: Cytokine Reference (eds. Oppenhein and Feldmann. pp. 3-20, 2001 Rao, et al, *Annual Rev. Immunol.* (1997) 15: 707.

Park et al.. "Targeting and Blocking B7 Costimulatory Molecules on Antigen-Presenting Cells Using CTLA4lg-Conjugated Liposomes: In Vitro Characterization and in Vivo Factors Affecting Biodistribution," *Pharm Res*. 20(8):1239-1248 (2003).

Pearson and Lipman, "Improved Tools for Biological Sequence Comparison," *Proc. Nat'l. Acad. Sci. USA* 85:2444-2448 (1988).

Porkka et al., "A Fragment of the HMGN2 Protein Homes to the Nuclei of Tumor Cells and Tumor Endothelial Cells in Vivo," *Proc Natl Acad Sci U S A*. 99(11):7444-7449 (2002).

Rao, et al., "Transcription Factors of the NFAT Family: Regulation and Function," *Annu. Rev. Immunol.* 15:707-747 (1997).

Schraa et al. "Endothelial Cells Internalize and Degrade RGD-Modified Proteins Developed for Tumor Vasculature Targeting," *J. Control Release* 83:241-251 (2002).

Seo et al., "Depletion of IL-10- and TGF-β-Producing Regulatory γs T Cells by Administering a Daunomycin-Conjugated Specific Monoclonal Antibody in Early Tumor Lesions Augments the Activity of CTLs and NK Cells," *J. Immunol.* 163:242-249 (1999).

Sharifi et al., "Generation of Human Interferon Gamma and Tumor Necrosis Factor Alpha Chimeric TNT-3 Fusion Proteins," *Hybridoma and Hybridomics* 21:421-432 (2002).

Sharifi et al., "Characterization of a Phage Display-Derived Human Monoclonal Antibody (NHS76) Counterpart to Chimeric TNT-1 Directed Against Necrotic Regions of Solid Tumors," *Hybridoma and Hybridomics* 20:305-312 (2001).

Silagi, et al., "Successful Immunotherapy of Mouse Melanoma and Sarcoma with Recombinant Interleukin-2 and Cyclophosphamide," *J. Biol. Response Modifiers* 5:411-422 (1986).

Smith and Waterman, "Comparison of Biosequences," *Adv. Appl. Math.* 2:482-489 (1981).

Smith, K.A., "Lowest Dose Interleukin-2 Immunotherapy," *Blood* 81:1414-1423 (1993).

Sone, et al., "Local Interleukin-2 Therapy for Cancer, and Its Effector Induction Mechanisms," *Oncology*, 51:170-176 (1994).

Stephens, et al., "Human CD4[+]CD25[+] Thymocytes and Peripheral T Cells Have Immune Suppressive Activity in Vitro," *Eur. J. Immunol.* 31:1247-1254 (2001).

Thelen, M., "Dancing to the Tune of Chemokines," *Nature Immunology*, 2:129-134 (2001).

Wilcox, et al., "Ligation of CD137 Receptor Prevents and Reverses Established Anergy of CD8[+] Cytolic T Lymphocytes in Vivo," *Blood* 103:177-184 (2004).

Zach-Howard, et al., "LEC Induces Chemotaxis and Adhesion by Interacting with CCR1 and CCR8," *Blood*, 96:840-845 (2000).

Presentation at the AACR 93rd Annual Meeting, San Francisco, CA, Apr. 6-10, 2002. Abstract No. 2789 of the presentation entitled: "LEC/chTNT-3 fusion protein for the immunotherapy of solid tumors" presented by Jiali Li during the meeting on Apr. 8, 2002, 1:00-5:00 p.m.

Challita-Eid et al. , "A RANTES—Antibody Fusion Protein Retains Antigen Specificity and Chemokine Function." J. Immunolo. (1996) 161(7):3729-3736.

"Research Presented in Mutliple Abstracts Extends Functions of Anticancer Technologies", Retrieved from the Internet: http://www.peregrineinc.com/content.php?mi=MTc=&appAction=—PRINT &Id=Mjc3MTcy, Apr. 2001 [Retrieved on Aug. 1, 2007], "the whole document".

(56) References Cited

OTHER PUBLICATIONS

Li Jiali et al:, "LEC/chTNT-3 fusion protein for the immunotherapy of solid tumors", American Association for Cancer Research, 93$^{rd}$ Annual Meeting, vol. 43, p. 562, 2002.

Shimizu et al., "Induction of Tumor Immunity by Removing CD25+CD4+ T Cells: A Common Basis Between Tumor Immunity and Autoimmunity", Journal of Immunology, 163(10): 5211-5218, 1999.

Steiz et al., "Depletion of CD25+ CD4+ T Cells and Treatment with Tyrosinase-related Protein 2-transduced Dendritic Cells Enhance the Interferon α-induced, CD8+ T-Cell-dependent Immune Defnse of B16 Melanoma", Cancer Research, 61(24): 8643-8646, 2001.

Sutmuller et al., "Synergism of Cytotoxic T Lymphocyte-associated Antigen 4 Blockade and Depletion of CD25+ Regulatory T Cells in Antitumor Therapy Reveals Alternative Pathways for Suppression of Autoreactive Cytotoxic T Lymphocyte Responses", J. Exp. Med., 194(6): 825-832, 2001.

Holzer et al, A Fusion Protein of IL-8 and a FAB Antibody Fragment Binds to IL-8 Receptors and Induces Neutrophil Activation, Cytokine, vol. 8, No. 3 Mar. 1996, pp. 214-221.

International Search Report dated Oct. 13, 2005 for PCT Application No. PCT/US2004/04116.

Khawli et al, Improving the chemotherapeutic index of IUdR using a vasoactive immunoconjugate, Radiochimica Acta., 79:83-86 (1997).

Mesh word search for RANTES (CCI5) 2009.

Mule et al, The Anti-Tumor Efficacy of Lymphoklne-Activated Killer Cells and Recombinant Interleukin 2 In Vivo: Direct Correlation Between Reduction of Established Metastases and Cytolytic Activity of Lymphokine-Activated Killer Cells, Anti-Tumor J Immunology, vol. 136, p. 3899-09, 1988.

Onizuka et al, Tumor Rejection by in Vivo Administration of Anti-CD25 (Interleukin-2 Receptor α) Monoclonal Antibody, Cancer Res, vol. 59, p. 3128-33, 1999.

Sequence search result. (2009).

Supplementary European Search Report dated May 11, 2007 for Application No. 04711085.3.

Youn et al, Isolation and characterization of LMC, a novel lymphocyte and nonocyte chemoattractant human CC chemokine, with myelosuppressive activity, Biochem. Biophys Res Commun., vol. 247, p. 217-222,1998.

English Abstract of JP 2002-519065.

Koh et al, Induction of tumor immunity by manipulating CD25 + CD4 + regulatory T cells, The Meeting of The Japanese Society for Immunology: The Record of Academic Conference, Japan, Oct. 31, 2002, vol. 32, p. 218, col. 3-A-W33-28-P.

Office Action dated Mar. 5, 2010 for JP Application No. 2006-503521 (with English Translation).

Shumizu et al., Induction of tumor immunity by manipulating regulatory T cells, The Record of Academic Conference of the Japan Cancer Association, Japan, Aug. 25, 2002, vol. 6lst. p. 41, col. 3014 (English Translation).

Yamazaki et al, Induction of tumor immunity by manipulating regulatory CD25 + CD4 + T cells, The Meeting of The Japanese Society for Immunology: The Record of Academic Conference, Japan, Sep. 26, 2000, vol. 30, p. 159, col. 2-C-142-P (English Translation).

Bauer, S. et al. (2009) "Sequential cancer immunotherapy: targeted activity of dimeric TNF and IL-8," Cancer Immunity, 9:2.

Morris, J.C. et al. (2000) "Advances in interleukin 2 receptor targeted treatment," Ann Rheum Dis, 59(suppl. I):109-114.

Notice of Allowance dated May 23, 2013 for U.S. Appl. No. 11/674,569, 9 pages.

Patent Board Decision on Appeal—Examiner Affirmed-in-Part dated Mar. 1, 2013 for U.S. Appl. No. 11/674,569, 16 pages.

Examiner's Answer to Appeal Brief dated Oct. 27, 2010 for U.S. Appl. No. 11/674,569, 26 pages.

Final Office Action dated Apr. 30, 2010 for U.S. Appl. No. 11/674,569, 18 pages.

Non-Final Office Action dated Jul. 10, 2009 for U.S. Appl. No. 11/674,569, 20 pages.

Restriction Requirement dated Mar. 2, 2009 for U.S. Appl. No. 11/674,569, 7 pages.

U.S. Appl. No. 13/865,902, filed Apr. 18, 2013, Epstein et al.

\* cited by examiner

FIG. 2
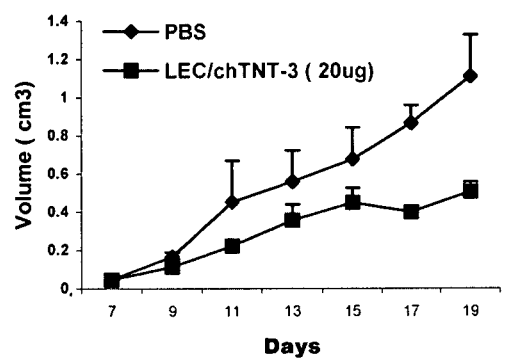
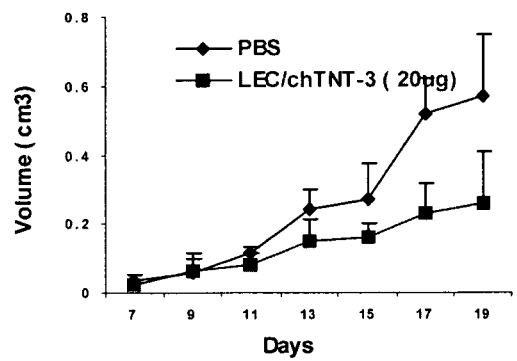

FIG. 7

Human LEC DNA Sequence (SEQ ID NO: 1)

```
  1  atgaaggtct  ccgaggctgc  cctgtctctc  cttgtcctca  tccttatcat  tacttcggct
 61  tctcgcagcc  agccaaaagt  tcctgagtgg  gtgaacaccc  catccacctg  ctgcctgaag
121  tattatgaga  aagtgttgcc  aaggagacta  gtggtgggat  acagaaaggc  cctcaactgt
181  cacctgccag  caatcatctt  cgtcaccaag  aggaaccgag  aagtctgcac  caacccaat
241  gacgactggg  tccaagagta  catcaaggat  cccaacctac  ctttgctgcc  taccaggaac
301  ttgtccacgg  ttaaaattat  tacagcaaag  aatggtcaac  cccagctcct  caactcccag
361  tga
```

FIG. 8

Human LEC Amino Acid Sequence

A. Precursor Protein (SEQ ID NO: 2)

MKVSEAALSLLVLILIITSASRSQPKVPEWVNTPSTCCLKYYEK
VLPRRLVVGYRKALNCHLPAIIFVTKRNREVCTNPNDDWVQEYIKDPNLPLLPTRNL
STVKIITAKNGQPQLLNSQ

B. Mature Protein (SEQ ID NO: 3)

QPKVPEWVNTPSTCCLKYYEK
VLPRRLVVGYRKALNCHLPAIIFVTKRNREVCTNPNDDWVQEYIKDPNLPLLPTRNL
STVKIITAKNGQPQLLNSQ

LEC/NHS76 Expression Vector

SEQUENCE LISTING

```
<160> NUMBER OF SEQ ID NOS: 6

<210> SEQ ID NO 1
<211> LENGTH: 363
<212> TYPE: DNA
<213> ORGANISM: Homo sapiens

<400> SEQUENCE: 1
atgaaggtct ccgaggctgc cctgtctctc cttgtcctca tccttatcat tacttcggct      60
tctcgcagcc agccaaaagt tcctgagtgg gtgaacaccc catccacctg ctgcctgaag     120
tattatgaga aagtgttgcc aaggagacta gtggtgggat acagaaaggc cctcaactgt     180
cacctgccag caatcatctt cgtcaccaag aggaaccgag aagtctgcac caaccccaat     240
gacgactggg tccaagagta catcaaggat cccaacctac ctttgctgcc taccaggaac     300
ttgtccacgg ttaaaattat tacagcaaag aatggtcaac cccagctcct caactcccag     360
tga                                                                    363

<210> SEQ ID NO 2
<211> LENGTH: 120
<212> TYPE: PRT
<213> ORGANISM: Homo sapiens

<400> SEQUENCE: 2

Met Lys Val Ser Glu Ala Ala Leu Ser Leu Leu Val Leu Ile Leu Ile
  1               5                  10                  15

Ile Thr Ser Ala Ser Arg Ser Gln Pro Lys Val Pro Glu Trp Val Asn
             20                  25                  30

Thr Pro Ser Thr Cys Cys Leu Lys Tyr Tyr Glu Lys Val Leu Pro Arg
         35                  40                  45

Arg Leu Val Val Gly Tyr Arg Lys Ala Leu Asn Cys His Leu Pro Ala
     50                  55                  60

Ile Ile Phe Val Thr Lys Arg Asn Arg Glu Val Cys Thr Asn Pro Asn
 65                  70                  75                  80

Asp Asp Trp Val Gln Glu Tyr Ile Lys Asp Pro Asn Leu Pro Leu Leu
```

```
                        85                  90                  95

Pro Thr Arg Asn Leu Ser Thr Val Lys Ile Ile Thr Ala Lys Asn Gly
            100                 105                 110

Gln Pro Gln Leu Leu Asn Ser Gln
        115                 120

<210> SEQ ID NO 3
<211> LENGTH: 97
<212> TYPE: PRT
<213> ORGANISM: Homo sapiens

<400> SEQUENCE: 3

Gln Pro Lys Val Pro Glu Trp Val Asn Thr Pro Ser Thr Cys Cys Leu
 1               5                  10                  15

Lys Tyr Tyr Glu Lys Val Leu Pro Arg Arg Leu Val Val Gly Tyr Arg
            20                  25                  30

Lys Ala Leu Asn Cys His Leu Pro Ala Ile Ile Phe Val Thr Lys Arg
        35                  40                  45

Asn Arg Glu Val Cys Thr Asn Pro Asn Asp Asp Trp Val Gln Glu Tyr
    50                  55                  60

Ile Lys Asp Pro Asn Leu Pro Leu Leu Pro Thr Arg Asn Leu Ser Thr
65                  70                  75                  80

Val Lys Ile Ile Thr Ala Lys Asn Gly Gln Pro Gln Leu Leu Asn Ser
                85                  90                  95

Gln

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tctagaatga aggtctccga ggctgcc                                             27

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcggccgcct gggagttgag gagctg                                              26

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 6

Gly Gly Gly Gly Ser
 1               5
```

COMPOSITIONS AND METHODS FOR CANCER IMMUNOTHERAPY

CROSS-REFERENCE TO RELATED PATENT APPLICATIONS

This application is a An application claiming the benefit under 35 USC 119(e) U.S. application Ser. No. 60/447,714, filed Feb. 14, 2003, incorporated herein by reference in its entirety.

FIELD OF THE INVENTION

The present invention relates to cancer therapeutic agents comprising a cancer targeting molecule and a liver expressed chemokine "LEC" and their use in the treatment of cancer.

BACKGROUND OF THE INVENTION

The following discussion of the background of the invention is merely provided to aid the reader in understanding the invention and is not admitted to describe or constitute prior art to the present invention.

Surgery, radiation therapy, and chemotherapy have been the standard accepted approaches for treatment of cancers including leukemia, solid tumors, and metastases. Immunotherapy (sometimes called biological therapy, biotherapy, or biological response modifier therapy), which uses the body's immune system, either directly or indirectly, to shrink or eradicate cancer has been studied for many years as an adjunct to conventional cancer therapy. It is believed that the human immune system is an untapped resource for cancer therapy and that effective treatment can be developed once the components of the immune system are properly harnessed. As key immunoregulatory molecules and signals of immunity are identified and prepared as therapeutic reagents, the clinical effectiveness of such reagents can be tested using well-known cancer models. Immunotherapeutic strategies include administration of vaccines, activated cells, antibodies, cytokines, chemokines, as well as small molecular inhibitors, anti-sense oligonucleotides, and gene therapy (Mocellin, et al., *Cancer Immunol. & Immunother.* (2002) 51: 583-595; Dy, et al., *J. Clin. Oncol.* (2002) 20: 2881-2894, 2002).

Cytokines are extracellular protein messenger molecules produced by cells involved in inflammation, immunity, differentiation, cell division, fibrosis, and repair (Smith, K. A.: *Blood* (1993) 81: 1414-1423). Cytokines such as such as TNFα, IL-1α, TGFβ, and CD40 ligand also function as cell surface signaling molecules. A characteristic of cytokines that distinguishes them from other natural bioactive molecules is that cytokines are generated in response to stimulation rather than being constitutively produced. Cytokine genes are highly inducible and their encoding mRNA levels subject to regulation by a transcriptional factors, such as NFκB, NF-AT, and AP-1 (Oppenheim, et al., "Introduction to the role of cytokines in innate host defense and adaptive immunity" In: Cytokine Reference (eds. Oppenhein and Feldmann. Pp 3-20, 2001)). Cytokine production generally lasts a few hours to a few days and has a short action radius. Thus, cytokines act mainly on neighboring cells rather then systemically. When administered systemically as a pharmaceutical, cytokines exhibit serious toxicity causing multiple symptoms including fever, hypotension, headache, malaise, and weakness. Toxicity makes is difficult to administer cytokines in clinically relevant dosages.

The first cytokine to obtain approval for cancer therapy is Interleukin-2 (IL-2) (Rao, et al, *Annual Rev. Immunol.* (1997) 15: 707-747). The primary role of IL-2 is to stimulate the growth and proliferation of T lymphocytes, however, it has stimulatory effects on a variety of other immune cells including natural killer (NK) cells, lymphokine-activated killer (LAK) cells, monocytes, and macrophages (Id.). While IL-2 has shown some promise in the treatment of renal cancer and melanomas (Silagi, et al., *J. Biol. Response Modifiers.* (1986) 5: 411-422), it has serious side affects including damage to the blood vessels of the body (capillary leak syndrome) that limit is usefulness for other cancers. Intratumoral administration of IL-2 is somewhat more effective than systemic administration (Silagi, et al., *J. Biol. Response Modifiers.* (1986) 5: 411-422; Sone, et al., *Oncology* (1994) 51: 170-176), however, intratumoral administration is not feasible for disseminated disease.

The concept of adoptive cellular therapy for tumors, first presented nearly 50 years ago by Mitchison (Mitchison, N. A.: *J Exp Med.* (1955) 102:157-77), has at its goal the elimination of cancer through the transfer of activated T-cells and/or natural killer cells. Adoptive immunotherapy is based on the belief that tumor specific cytotoxic T-cells are present in cancer patients, but that such cells have not been primed and/or that the in vivo function of the cells is impaired. To prime the cells, peripheral T-cells are removed from the patient, activated ex vivo, and then re-infused. The step of ex vivo activation also may include exposure to the patient's tumor cells or to a tumor cell vaccine. Although T-cell based adoptive immunotherapy provides a potentially promising form of cancer treatment, it has failed to induce a long-lasting response in the majority of patients who have received this therapy (Lum, et al., *J Immunother.* (2001) 24:408-19).

Although much has been learned about controlling and directing an immune response, there is need for newer and more effective immunotherapeutic approaches to cancer therapy.

SUMMARY OF THE INVENTION

In one aspect, the present invention provides a cancer therapeutic agent comprising a cancer targeting molecule linked to a liver-expressed chemokine (LEC).

In one embodiment, the cancer targeting molecule is an antibody that targets cancer cells or tumors in vivo. In another embodiment, the antibody is specific for a tumor cell-surface antigen. In yet another embodiment, the antibody is specific for a stromal component of a tumor. In still yet another embodiment, the antibody is specific for an intracellular antigen, such as an intranuclear antigen(s). In the latter case, the antibody may be a humanized or human chimeric antibody based on the murine antibody TNT-1, TNT-2, TNT-3 or NHS76.

The linkage between the cancer targeting molecule and LEC may be through covalent or non-covalent association. The cancer targeting molecule and LEC may be covalently associated by chemical cross-linking or through genetic fusion such as by application of recombinant DNA techniques. In the latter approach, LEC may be fused at its C-terminus or N-terminus to the N-terminus or C-terminus of the protein cell targeting molecule. When the cell targeting molecule is an antibody, the C-terminus of LEC is preferably fused to the N-terminus of the light and/or heavy chain of the antibody.

The cancer therapeutic agent of the invention can be used for treatment of cancer in an individual so afflicted. Accordingly, another aspect of the present invention is a method of reducing the size of a tumor or inhibiting the growth of cancer cells in an individual comprising administering an effective amount of a cancer therapeutic agent of the invention, wherein the agent localizes to the cancer cells or tumor in the individual.

A further aspect of the invention is a method of reducing or inhibiting the development of metastatic cancer, comprising administering an effective amount of a cancer therapeutic agent of the invention, wherein the cancer therapeutic agent localizes to cancer cells or tumor in the individual.

In one embodiment, the effectiveness of the therapy using the invention cancer therapeutic agents may be increased by reducing the activity of immunoregulatory T cells in the individual. This may be achieved by removing ex vivo or depleting or inactivating in vivo immunoregulatory T cells characterized in suppressing the host anti-tumor immune response. In one embodiment, immunoregulatory T cells may be removed or depleted or inactivated using at least one antibody that binds to the immunoregulatory T cells. The antibody may bind to the IL-2 receptor, preferably to CD25. The activity of immunoregulatory T cells may be reduced in the individual before, during or after administering the invention cancer therapeutic agent.

In another embodiment, treatment with the invention cancer therapeutic agents may also include adoptive transfer of immune cells. These immune cells are preferably T cells, which may be activated ex vivo. In one embodiment, activation is achieved by exposure to IL-2 and/or anti-CD3 antibody. In another embodiment, ex vivo activation is achieved by exposure to the cancer cells or to a cancer cell vaccine. Adoptive transfer of immune cells may occur before, during or after administering the invention cancer therapeutic agent. In some embodiments, adoptive transfer may be combined with reducing the activity of immunoregulatory T cells in the individual. In this case, the adoptive transfer is preferably given after removal, depletion or inactivation of immunoregulatory T cells.

BRIEF DESCRIPTION OF THE FIGURES

FIG. 2. LEC/chTNT-3 immunotherapy of two murine solid tumors.

FIG. 7. Nucleotide sequence of an exemplary human LEC (SEQ ID NO:1).

FIG. 8. Amino acid sequence of an exemplary human LEC precursor (SEQ ID NO: 2) and mature (SEQ ID NO: 3) chemokine.

DETAILED DESCRIPTION OF THE INVENTION

Figure 1:
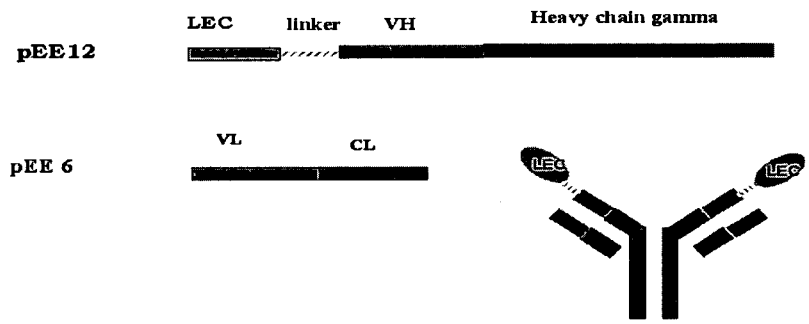
FIG. 1. Schematic diagram demonstrating the construction of LEC/chTNT-3. A Gly$_4$Ser linker (SEQ ID NO: 6) is located between the LEC gene and the chTNT-3 heavy chain variable region.

In accordance with one aspect of the invention, cancer therapeutic agents are provided which comprise a cancer targeting molecule linked to a "LEC" chemokine. Such invention cancer therapeutic agents (i.e. LEC cancer therapeutic agents) are useful for cancer therapy in accordance with the methods of the invention.

The term "cancer targeting molecule" refers to a molecule that has the ability to localize to cancer cells in vivo. The phrase "localizing to cancer cells in the individual" (i.e., "in vivo") means that the agent can bind to a tumor cell(s) or can bind in the vicinity of a tumor cell(s). The cancer targeting molecule may bind to a receptor or ligand on the surface of the cancer cell or may bind to an intracellular target of cancer cell provided that the target is accessible to the agent. Accessibility to intracellular cancer cell targets may arise in cancer cells that have a compromised plasma membrane such as cells which are undergoing apoptosis, necrosis, and the like. For example, certain cancer targeting molecules can bind intracellular portions of a cell that does not have a compromised plasma membrane. See e.g., Porkka et al., *Proc Natl Acad Sci USA.* (2002) 99(11): 7444-9.

Cancer targeting molecules also may bind to a molecule that is present in the tumor. As used herein "tumor" includes cancer cells, necrosis, as well as stroma. Stroma includes cells such as fibroblasts and endothelial cells of vessels and capillaries and extracellular matrix, which is composed of fibrillar and non-fibrillar components. The major fibrillar proteins are collagen and elastin. A cancer targeting molecule may target to the tumor by binding to the stroma which surrounds the cancer cells in the tumor. Thus, a cancer targeting molecule may target in the vicinity of a cancer by binding to a stromal component such as a fibroblast or endothelial cell or a component of the extracellular matrix. See, e.g. Schraa et al. *Control Release* (2002) 83(2): 241-51; Arap et al. *Haemostasis* (2001) 31 Suppl 1: 30-1.

Cancer targeting molecules useful in the present invention include those that bind to tumor specific or tumor associated antigens. The term "tumor associated antigen" (TAA) as used herein refers to a protein which is present on tumor cells, and on normal cells during fetal life (onco-fetal antigens), after birth in selected organs, or on normal cells, but at much lower concentration than on tumor cells. A TAA also may be present in the stroma in the vicinity of the cancer cell but be expressed at lower amounts in the stroma elsewhere in the body. A variety of TAA have been described including BRCA-1 and BRCA-2 proteins, the HER-2-neu, mucins such as MUC1, integrins, cytokines, and the like. In contrast, tumor specific antigen (TSA) (aka. "tumor-specific transplantation antigen" or TSTA) refers to a tumor cell expressed protein absent from normal cells. TSA usually appear when an infecting virus has caused the cell to become immortal and to express virus antigens. Exemplary viral TSAs are the E6 or E7 proteins of HPV type 16. TSAs not induced by viruses can be idiotypes of the immunoglobulin on B cell lymphomas or the T cell receptor (TCR) on T cell lymphomas.

Cancers treatable using the methods of the invention include carcinomas, sarcomas, and leukemias and lymphomas and other types of cancer. Carcinomas include those of lung, breast, colon, ovarian, prostate, and the like. These cancers may be primary or metastatic. In the case of leukemias and lymphomas, the cancer cells treatable with the invention methods include those in the form of a tumor as well as cancer cells in the bone marrow and in the circulation.

Cancer targeting molecules include small molecule compounds such as drugs, organic compounds, peptides, peptidomimetics, as well as larger molecules such as glycoproteins, proteoglycans, lipids glycolipids, phospholipids, lipopolysaccharide, nucleic acids, proteoglycans, carbohydrates, and the like. Small molecule cancer targeting molecules may be about 5,000 daltons or less in size. Cancer targeting molecules may include well known therapeutic compounds including anti-neoplastic agents. Anti-neoplastic targeting molecules may include paclitaxel, daunorubicin, doxorubicin, carminomycin, 4'-epiadriamycin, 4-demethoxy-daunomycin, 11-deoxydaunorubicin, 13-deoxydaunorubicin, adriamycin-14-benzoate, adriamycin-14-octanoate, adriamycin-14-naphthaleneacetate, vinblastine, vincristine, mitomycin C, N-methyl mitomycin C, bleomycin A2, dideazatetrahydrofolic acid, aminopterin, methotrexate, cholchicine and cisplatin, and the like. Cancer targeting molecules also may include toxins such as diphtheria toxin, cytokines such as CSF, GSF, GMCSF, TNF, erythropoietin, immunomodulators or cytokines such as the interferons or interleukins, a neuropeptide, reproductive hormone such as HGH, FSH, or LH, thyroid hormone, neurotransmitters such as acetylcholine, and hormone receptors such as the estrogen receptor.

Cancer targeting molecules can be a protein or peptide. "Polypeptide", "peptide," and "protein" are used interchangeably to refer to a polymer of amino acid residues linked by amide bonds. As used herein, these terms apply to amino acid polymers in which one or more amino acid residue is an artificial chemical analogue of a corresponding naturally occurring amino acid. Thus, proteins may include natural and non-natural amino acids. Amino acids can be in the L or D form as long as the binding function of the peptide is maintained. Peptides can be of variable length, but are generally between about 4 and 200 amino acids in length. Peptides may be cyclic, having an intramolecular bond between two non-adjacent amino acids within the peptide, e.g., backbone to backbone, side-chain to backbone and side-chain to side-chain cyclization. Cyclic peptides can be prepared by methods well know in the art. See e.g., U.S. Pat. No. 6,013,625.

The cancer targeting molecule may be an antagonist or agonist of an integrin. Integrin is a heterodimeric transmembrane glycoprotein complex that functions in cellular adhesion events and signal transduction processes. Integrins, which comprise and alpha and a beta subunit, include numerous types including $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_7\beta_1$, $\alpha_8\beta_1$, $\alpha_9\beta_1$, $\alpha_1\beta_1$, $\alpha_6\beta_4$, $\alpha_4\beta_7$, $\alpha_D\beta_2$, $\alpha_D\beta_2$, $\alpha_L\beta_2$, $\alpha_M\beta_2$, $\alpha_v\beta_1$, $\alpha_v\beta_3$, $\alpha_v\beta_5$, $\alpha_v\beta_6$, $\alpha_v\beta_8$, $\alpha_x\beta_2$, $\alpha_{11b}\beta_3$, $\alpha_{IELb}\beta_7$, and the like. Integrin $\alpha_v\beta_3$ is expressed on a variety of cells and has been shown to mediate several biologically relevant processes, including adhesion of osteoclasts to bone matrix, migration of vascular smooth muscle cells, and angiogenesis. Suitable targeting molecules for integrins include RGD peptides or peptidomimetics or non-RGD peptides or peptidomimetics (see, e.g., U.S. Pat. Nos. 5,767,071 and 5,780,426) as well as for other integrins such as $\alpha_4\beta_1$ (VLA-4), $\alpha_4\beta_7$ (see, e.g., U.S. Pat. No. 6,365,619; Chang et al., *Bioorganic & Medicinal Chem Lett,* 12:159-163 (2002); Lin et al., *Bioorganic & Medicinal Chem Lett,* 12:133-136 (2002)), and the like.

A preferred cancer targeting molecule is an antibody. The term "antibody" as used herein includes immunoglobulins, which are the product of B cells and variants thereof as well as the T cell receptor (TcR), which is the product of T cells, and variants thereof. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of IgG1, IgG2, IgG3 and IgG4 subclass.

A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as full length intact antibodies or as a number of well-characterized fragments produced by digestion with various peptidases or chemicals. Thus, for example, pepsin digests an antibody below the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region thereby converting the F(ab')2 dimer into an Fab' monomer. The Fab' monomer is essentially a Fab fragment with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that any of a variety of antibody fragments may be synthesized de novo either chemically or by utilizing recombinant DNA methodology. Thus, the term antibody, as used herein also includes antibody fragments either produced by the modification of whole antibodies or synthesized de novo or antibodies and fragments obtained by using recombinant DNA methodologies.

Recombinant antibodies may be conventional full length antibodies, antibody fragments known from proteolytic digestion, unique antibody fragments such as Fv or single chain Fv (scFv), domain deleted antibodies, and the like. Fragments may include a domains or polypeptides with as little as one or a few amino acid deleted or mutated while more extensive deletion is possible such as deletion of one or more domains.

An Fv antibody is about 50 Kd in size and comprises the variable regions of the light and heavy chain. A single chain Fv ("scFv") polypeptide is a covalently linked VH::VL heterodimer which may be expressed from a nucleic acid including VH- and VL-encoding sequences either joined directly or joined by a peptide-encoding linker. See Huston, et al. (1988) *Proc. Nat. Acad. Sci.* USA, 85:5879-5883. A number of structures for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513, 5,132,405 and 4,956,778.

An antibody may be a non-human antibody, a human antibody, a humanized antibody or a chimeric antibody, the latter comprising human and non-human antibody sequence. As is known in the art, chimeric antibody is prepared by exchanging a non-human constant region (heavy chain, light chain or both) with a human constant region antibody. See e.g. U.S. Pat. No. 4,816,567 to Cabilly et al. Methods of making humanized antibodies from non-human antibodies such as from murine antibodies are also well known (see, e.g., U.S. Pat. No. 5,565,332 to Winter).

A cancer targeting molecule may be an antibody that targets to a nuclear antigen that is accessible in necrotic portions of a tumor. Necrotic cell targeting also known as Tumor Necrosis Therapy (TNT) (Ref. no. 1-5, 7, 8) represents a different approach from methods that employ antibodies that bind to tumor-associated cell surface antigens and require the use of different antibodies for each type of tumor. TNT antibodies bind intracellular antigens found in all cells and which are retained by dying cells and which show preferential localization in malignant tumors due to the presence of abnormally permeable, degenerating cells only rarely present in normal tissues. Rapidly dividing tumors contain a proportion of degenerating or dead cells, but, with attention focused upon attempts to kill the dividing cells, the degenerating component has largely been ignored. Calculations of tumor cell loss have revealed that, in contrast to normal tissues, 30-80% of the progeny of tumor cell divisions shortly undergo degeneration. In tumors, the imperfect vasculature and impaired phagocytic response, permit the accumulation of degenerating cells, often with the formation of large areas of necrosis, long recognized by pathologists to be a typical feature of malignant tumors (Epstein, et al., *Cancer Res* (1988) 48:5842-5848). Thus, the accumulation within tumors of a high proportion of dying cells constitutes a major distinction between malignant tumors and normal tissues wherein sporadic cell death occurs at a relatively low rate and is accompanied by a rapid (within minutes) and orderly removal of necrotic elements from the tissue. Since degenerating cells have a permeable cell surface membrane not observed in viable cells, TNT antibodies enter and bind to their intracellular antigens in necrotic areas of the tumor. Contrarily, TNT antibodies diffusing in viable regions of the tumor and normal tissues do not bind and are removed from the circulation by normal clearance mechanisms. Hence, TNT antibodies provide a useful approach for specifically targeting necrotic regions of tumors and can be used to deliver diagnostic and therapeutic reagents into these regions which are may be situated deep within the central core of tumors. TNT antibodies have a number of unique features that distinguishes from other forms of antibody therapy. Because of these attributes, TNT antibodies have several advantages that enable the delivery of radionuclides (Ref. no. 5,7), immunostimulatory molecules (Ref. no. 9-11), and vasopermeability agents (Ref. no. 12-15) for the treatment of cancer.

As discussed, the cancer therapeutic invention compositions comprise a LEC chemokine. Chemokines are small (7-16 kD), secreted, and structurally related soluble proteins that are involved in leukocyte and dendritic cell chemotaxis, PMN degranulation, and angiogenesis (Mackay C R. *Nature Immunol.* (2001) 2:95-101; Gerard, et al., *Nature Immunol.* (2001) 2:108-115). Chemokines are produced during the initial phase of host response to injury, allergens, antigens, or invading microorganisms. Chemokines selectively attract leukocytes to inflammatory foci, inducing both cell migration and activation. To function, chemokines are elaborated principally at the site of injury or infection and have a very short half-life due to their small size. Since systemic administration is associated with severe side effects (6), it is difficult to obtain high local concentrations of chemokines in tumors in order to achieve an effective immune response.

Chemokines have been classified into the alpha (C—X—C), beta (C—C), and the gamma (C) subgroups based upon the positioning of cysteine residues near the C terminus, some of which participate in the formation of an intrachain S—S bridge. The α chemokines have a single amino acid inserted between the first and second of their four cysteine residues, whereas these cysteines are not separated in the β group. The γ chemokines have only one pair of cysteines. Due to their important role in the immune system, chemokines have been utilized to treat inflammatory and autoimmune diseases (Vaddi, et al., *The Chemokine facts book* 1997), HIV (Baroudy B M. "A Small molecule antagonist of CCR5 that effectively inhibits HIV-1 potential as a novel antiretroviral agent." 7th Conference on Retroviruses and Opportunistic Infections, 2000), and cancer (Miyagishi, et al., *J Neuro Sci.* (1995)).

The mechanism of chemokine action involves initial binding to various transmembrane spanning G protein-linked receptors on target cells. The interaction of chemokines with these G protein-linked receptors causes a rapid reconfiguration of adhesion proteins, such as β integrins, on the surface of the responding cells, facilitating their adhesion to endothelial cells (EC) lining blood vessel walls. This adhesion is followed by leukocyte transmigration between the EC into the tissues. Once there, the inflammatory leukocytes migrate along a gradient of increasing concentration of the chemokine to the site of origin. In response to the higher chemokine concentration at the site of injury or microbial invasion, the leukocytes are activated to perform effector functions such as release of their granule contents and increased production of cytokines. LEC binds to and activates CCR1 and CCR8 chemokine receptors.

"Liver Expressed Chemokine" or "LEC" (CCL16), also known as NCC-4, LMC, and HCC-4, LCC-1 and monotactin-1, was originally found in an expression sequence tag library and later mapped to chromosome 17q in the CC chemokine cluster (Naruse, et al., *Genomics* (1996) 34:236-240). LEC is present in the plasma samples from healthy adult donors at relatively high concentrations (0.3-4 nM). The human gene encoding LEC has a length of approximately 5 kb and possesses three exons. Two types of transcripts, (579 bp, 1503 bp) are generated through alternative polyadenylation sites. The LEC gene in the mouse is a pseudogene that has lost its function due to the insertion of an intron (Id.).

The DNA sequence encoding human LEC includes 363 bases beginning at the ATG codon and including the stop codon (TGA) (see FIG. 7; SEQ ID NO: 1). The DNA encodes a human LEC precursor of 120 amino acids (FIG. 8; SEQ ID NO: 2), the first 23 representing a signal peptide which is cleaved during expression to yield the mature human LEC protein (FIG. 8; SEQ ID NO: 3).

LEC is a potent chemotactic factor for both human monocytes and dendritic cells (APC cells) (Moser, et al., *Nature Immunology* (2001) 2:123-128; Thelen, M.: *Nature Immunology* (2001) 2:129-134). LEC mediates its activity through the CCR1 and CCR8 chemokine receptors (Howard, et al., *Blood* (2000) 96:840-845). LEC binds consistently, binds with relatively low affinity, to CCR1, CCR2 and CCR5 receptors (Nomiyama et al. *Int Immunol.* (2001) 13(8): 1021-9). Human liver hepatocytes strongly express LEC as do human hepatocyte cell lines such as HepG2.

LEC is unique among chemokines, in having its mRNA levels increase and stabilize following treatment of cells with IL-10. In vitro studies indicate that LEC requires a much higher concentration to induce maximum chemotaxis than it does for adhesion (Id). The potential therapeutic applications of LEC have been studied by Giovarelli et al. (Ref. no. 6), who showed that mammary carcinoma TSA cells engineered to express LEC inhibit the metastatic spread of tumor and induce tumor rejection due to an impressive infiltration of macrophages, dendritic cells, T cells, and PMNs and the production of IFN-γ and IL-12. Rejection of tumor by the secretion of LEC involves both CD8$^+$ lymphocytes and polymorphonuclear leukocytes (Ref. no. 6). In these mice, an anti-tumor immune memory was quickly established after rejection as shown by TSA tumor challenge.

The term "LEC" as used herein includes amino acid sequences that are substantially similar or include conservative variations of the human LEC protein sequence. The terms "substantially similar" and "conservative variation" denotes the replacement of an amino acid residue by another biologically similar residue. Examples of conservative variations include the substitution of one hydrophobic residue such as isoleucine, valine, leucine or methionine for another, or the substitution of one polar residue for another, such as the substitution of arginine for lysine, glutamic acid for aspartic acid, or glutamine for asparagine, and the like. The terms "conservative variation" and "substantially similar" also include the use of a substituted amino acid in place of an unsubstituted parent amino acid provided that antibodies raised to the substituted polypeptide also immunoreact with the unsubstituted polypeptide.

LEC proteins that are substantially similar to the human LEC protein may substitute for human LEC in the cancer therapeutic compositions of the invention. Substantially similar LEC proteins share at least 75%, at least 80%, at least 85%, at least 90%, at least 95% and more preferably at least 98% sequence identity (i.e., homology) with the native human LEC sequence. Proteins which are substantially similar to the human LEC amino acid sequence and which are considered "LEC" proteins as this term is used herein also share at least one biological property with that of human LEC. Biological properties of LEC include binding to the chemokine receptors CCR1 or CCR8, or functioning as a chemoattractant for monocytes, lymphocytes, or PMNs. In this regard, LEC induces calcium mobilization and chemotaxis via CCR1 and CCR2. LEC also induces calcium mobilization, but marginal chemotaxis via CCR5.

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Methods of alignment of sequence for comparison are well-known in the art. Optimal alignment of sequences for comparison can be conducted, e.g., by the local homology algorithm of Smith and Waterman (1981, Adv. Appl. Math. 2:482) by the homology alignment algorithm of Needleman and Wunsch, (1970, J. Mol. Biol. 48:443) by the search for similarity method of Person and Lipman (1988, Proc. Nat'l. Acad. Sci. USA 85:2444) by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biologicalal Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. For example, a substantial portion of the human genome sequence is available for searching via the BLAST search tool at the National Center for Biotechnology Information (NCBI). Information about multiple sequenced genomes and the resources to analyze them also is available from NCBI on its Genomic Biology web page.

One example of a useful algorithm is BLAST (e.g., BLAST 2.0), which is described in Altschul et al., 1977, *Nucl. Acids Res.* 25:3389-3402, and Altschul et al., J. Mol. Biol., 1990 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra, 1977 and 1990). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment.

The BLASTN program (for nucleotide sequences) uses as defaults a word length (W) of 11, an expectation (E) of 10, $M=5$, $N=-4$ and a comparison of both strands. For amino acid sequences, the BLASTP program uses as defaults a word length of 3, and expectations (E) of 10, and the BLOSUM62 scoring matrix (see Henikoff and Henikoff, *Proc. Natl. Acad. Sci.* USA (1989) 89:10915) alignments (B) of 50, expectation (E) of 10, $M=5$, $N=-4$, and a comparison of both strands.

The BLAST algorithm also performs a statistical analysis of the similarity between two sequences (see, e.g., Karlin and Altschul, 1993, Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one aspect, the cancer therapeutic agent is not LEC/chTNT-3. As used herein, the term "LEC/chTNT-3" refers to a fusion protein comprising the native LEC sequence fused at its C-terminus via a specified peptide linker to the N-terminus of human/mouse chimeric TNT-3 heavy chain. The preparation of this fusion protein is described in Example 3.

Cancer therapeutic invention compounds comprise a cancer targeting molecule linked to LEC. The cancer targeting molecule and the chemokine may be linked covalently or non-covalently. As used herein, "linked" means that under physiological conditions of pH, ionic strength and osmotic potential, the majority of the entities are associated with each other at equilibrium. Covalent linkage may be by any of a variety of chemical crosslinking agents including, for example, homobifunctional or heterobifunctional crosslinking reagents, many of which are commercially available (see, e.g., Pierce Chemical Co. or Sigma Chemical Co.). Crosslinking can be achieved by any of a variety of chemistries well known in the art including, for example, activated polyethylene glycols, aldehydes, isocyanates, maleimides and the like.

The cancer targeting molecule may be linked to the chemokine through genetic fusion and may include a polypeptide linker sequence between the cancer targeting molecule and the chemokine. The composition and length of the linker may be determined in accordance with methods well known in the art and may be tested for efficacy. The linker is generally from about 3 to about 15 amino acids long, more preferably about 5 to about 10 amino acids long, however, longer or shorter linkers may be used or the linker may be dispensed with entirely. A Gly$_4$Ser linker (SEQ ID NO: 6) is an exemplary linker. Additional sequences may also be included to incorporate a cleavage site to separate the cancer targeting molecule from LEC at some later time. Thus, the linker may include a sequence that is a substrate for enzyme cleavage, e.g., an endopeptidase recognition sequence.

A protein based cancer targeting molecule, LEC or a targeting molecule-LEC fusion protein may be prepared using recombinant expression methods such as in prokaryotic or eukaryotic cells as is well known in the art. (see e.g., U.S. Pat. Nos. 5,116,943 and 6,331,415). In general, nucleic acid encoding the protein can be cloned into an expression vector for high yield expression of the encoded product. The expression vector can be part of a plasmid, virus, or may be a nucleic acid fragment. The expression vector includes an expression cassette into which the nucleic acid encoding the protein is cloned in operable association with a promoter and optionally an enhancer. The expression cassette may also include other features such as an origin of replication, and/or chromosome integration elements such as retroviral LTRs, or adeno associated viral (AAV) ITRs. If secretion of the protein is desired, DNA encoding a signal sequence may be placed upstream of the nucleic acid encoding the mature amino acids of the protein. DNA encoding a short protein sequence that could be used to facilitate later purification (e.g., a histidine tag) or assist in labeling the protein may be included within or at the ends of the protein encoding nucleic acid.

LEC may be fused from its N-terminus or C-terminus directly or indirectly to the C-terminus or N-terminus of a protein type cancer targeting molecule, provided the targeting molecule and LEC retain their essential biological activity. In some cases, LEC is preferably fused at its C-terminus to the N-terminus of a protein type cancer targeting molecule. In the case where cancer targeting molecule is an antibody, LEC may be fused to the N-terminus of the light and/or heavy chain of the antibody.

Cells suitable for replicating and for supporting recombinant expression of protein are well known in the art. Such cells may be transfected or transduced as appropriate with the particular expression vector and large quantities of vector containing cells can be grown for seeding large scale fermenters to obtain sufficient quantities of the protein for clinical applications. Such cells may include prokaryotic microorganisms, such as E. coli, or various other eukaryotic cells, such as Chinese hamster ovary cells (CHO), insect cells, or the like. Standard technologies are known in the art to express foreign genes in these systems.

The invention cancer therapeutic agents can be used for treatment of cancer in an individual so afflicted. Accordingly, another aspect of the present invention is a method of reducing the size of a tumor or inhibiting the growth of cancer in an individual comprising administering an effective amount of the invention composition wherein the cancer therapeutic agent localizes to cancer cells or tumor in the individual. A further aspect of the invention is the a method of inhibiting the development of metastasis in an individual suffering from cancer, comprising administering an effective amount the invention composition, wherein the cancer therapeutic agent localizes to metastatic cancer cells in the individual.

The effectiveness of treatment using the invention cancer therapeutic agents may be increased by reducing the activity of immunoregulatory T cells in the individual. This may be achieved by removing ex vivo or by depleting or inactivating immunoregulatory T cells in the individual. The term "immunoregulatory T cells" as used herein refers to a population of T cells that function, directly or indirectly, to suppress the host anti-tumor immune response. Immunoregulatory T cells may be CD4$^+$, CD25$^+$ or positive for both markers.

The term "removing ex vivo" as used herein with reference to immunoregulatory T cells means that immunoregulatory T cells are removed from the circulation of an individual by an ex vivo method, such as flow cytometric cell separation, column or filter separation and the like. The column or filter may have bound thereto an antibody that can bind to immunoregulatory T cells. Antibodies that bind to immunoregulatory T cells also may be used to identify such cells for removal by a flow cytometric device. Antibody suitable for binding to immunoregulatory T cells include antibody specific for the CD4 antigen, the alpha chain subunit of the IL-2 receptor (i.e. CD25), and the like. A combination of anti-T cell antibodies also may be used. Daclizumab®, a humanized monoclonal antibody that binds to CD25 or Basiliximab®, a chimeric version of this same antibody is commercially available from Novartis Pharma AG. Hu-Max-CD4®, a fully humanized antibody against CD4 also is commercially available (GenMab).

The term "depleting or inactivating in vivo immunoregulatory T cells" as used herein refers to a reduction in the ability of immunoregulatory T cells to suppress the host anti-tumor immune response following the administration of a pharmaceutical agent to the host. The pharmaceutical agent is one that when administered causes a loss of immunoregulatory T cells (i.e., depletion) or inactivation of anti-tumor immune suppression function of the immunoregulatory T cells.

Depleting or inactivating immunoregulatory T cells may be achieved by administering a pharmaceutical agent such as an antibody specific for the CD4 antigen, the alpha chain subunit of the IL-2 receptor (i.e. CD25), and the like, as described above. Also, an antibody to gamma delta immunoregulatory T cells can be used to deplete such cells and stimulate anti-tumor immunity as described previously. Seo et al., *J. Immunol.* (1999) 163:242-249. Anti-CD40 ligand, also may be used to deplete or inactivate immunoregulatory T cells.

Partial antibody constructs such as CTLA4Ig, a fusion protein of CTLA-4 and Fc of immunoglobulin (Ig) heavy chain, can be used to inhibit the essential costimulatory signal for full T cell activation via blocking the interaction between CD28 and B7 molecules. CTLA4Ig may be administered as a pharmaceutical to render regulatory T cells nonresponsive (i.e. inactivation). See Park et al. *Pharm Res.* (2003) 20(8): 1239-48. An IL-2 fusion to pseudomonas exotoxin (OnTac) is yet another reagent for depleting or inactivating regulatory T cells.

In another approach, agents may be administered that prevent the induction of CD8+ cytolytic T-lymphocyte (CTL) tumor anergy. Agents that agonize CD137, such as agonistic antibodies, may be used to restore the tumor cytolytic function of established anergic CTLs upon reencountering their cognate antigen. See Wilcox et al., *Blood* (2004) 103:177-184. This approach can be used to break T-cell tolerance to tumor antigens.

Agents that agonize glucocorticoid-induced tumor necrosis factor receptor ligand on CD4/CD25+ immunoregulatory T cells reverses the suppressive action of these cells (GITR). Tone et al., PNAS (2003) 100:15059-15064.*

Methods of removing, depleting or inactivating in vivo immunoregulatory T cells may be used even if the methods remove cells other than immunoregulatory T actively suppressing the host anti-tumor immune response. Effort to remove, deplete or inactivate immunoregulatory T cells may be performed multiple times during a given period of treatment. Also, different methods may be used together (e.g., ex vivo cell removal and in vivo depletion or inactivation). The amount of anti-T cell antibody administered for depletion or inactivation may be similar to the amount used in the transplantation field. See, e.g., Meiser et al., Transplantation. (1994) 27; 58(4): 419-23. Anti-CD40 ligand.

Immunoregulatory T cells may be depleted or inactivated before, during and/or after administration of the invention cancer therapeutic agents. Immunoregulatory T cells are preferably depleted before administering the invention cancer therapeutic agents.

In a further embodiment, the invention methods for cancer therapy may include adoptive transfer to immune cells to enhance anti-tumor immunity. As used herein "adoptive transfer" refers to the administration of immune cells, from another individual or from the same individual. These are preferably T cells, which may be activated ex vivo to enhance their ability to function in supporting an anti-tumor immune response. Adoptively transferred immune cells may be activated ex vivo by any of a variety of well known agents including, for example, exposure to IL-2 and/or to anti-CD3 antibodies. Ex vivo activation also may include exposure to a cancer cell vaccine. Such cancer cell vaccine may constitute live (but non-replicating), or killed cancer cells from the individual to be treated or from another cancer entirely. The vaccine also may be a cancer cell extract or purified vaccine preparation derived from cancer cells. Cancer cell vaccines are well known in the art and may be prepared in accordance with well known methods.

Adoptively transferred T cells may be administered before, during and/or after administration of the cancer targeting molecule invention composition. Adoptively transferred T cells are preferably given after administration of the cancer targeting molecule invention composition. In this form of therapy, patients receive multiple infusions of T-cells after ex vivo stimulation with IL-2 (Lum, et al., *J Immunother.* (2001) 24:408-19) or other agents such as anti-CD3$^+$ and anti-CD28$^+$ antibodies (June, C. H.: *J. Immunother* (2001) 24(5): 389-391).

In some embodiments, the effectiveness of the therapy using the invention cancer therapeutic agents can be increased by combining the approach of ex vivo removal and/or in vivo depleting or inactivating immunoregulatory T cells with adoptive transfer of immune cells. In such embodiments it may be advantageous to adoptively transfer after the step of removing, depleting or inactivating immunoregulatory T cells.

The invention cancer therapeutic agents can be administered as a pharmaceutical or medicament formulated with a pharmaceutically acceptable carrier. Accordingly, the compounds may be used in the manufacture of a medicament or pharmaceutical composition. Pharmaceutical compositions of the invention may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, sodium citrate, and the like.

Alternately, compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation may be in the form of a syrup, elixir, emulsion, or an aqueous or non-aqueous suspension. For rectal administration, the invention compounds may be combined with excipients such as cocoa butter, glycerin, gelatin or polyethylene glycols and molded into a suppository.

Compounds of the invention may be formulated to include other medically useful drugs or biological agents. The compounds also may be administered in conjunction with the administration of other drugs or biological agents useful for the disease or condition to which the invention compounds are directed.

As employed herein, the phrase "an effective amount," refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific compound, the route of administration, the rate of clearance of the compound, the duration of treatment, the drugs used in combination or coincident with the compound, the age, body weight, sex, diet, and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. Dosage levels typically fall in the range of about 0.001 up to 100 mg/kg/day; with levels in the range of about 0.05 up to 10 mg/kg/day are generally applicable. A compound can be administered parenterally, such as intravascularly, intravenously, intraarterially, intramuscularly, subcutaneously, or the like. Administration can also be orally, nasally, rectally, transdermally or inhalationally via an aerosol. The composition may be administered as a bolus, or slowly infused.

A therapeutically effective dose can be estimated initially from cell culture assays by determining an IC50. A dose can then be formulated in animal models to achieve a circulating plasma concentration range that includes the IC50 as determined in cell culture. Such information can be used to more accurately determine useful doses in humans. Levels in plasma may be measured, for example, by HPLC. The exact formulation, route of administration and dosage can be chosen by the individual physician in view of the patient's condition.

The administration of the invention cancer therapeutic agents to an immunocompetent individual may result in the production of antibodies against the cancer targeting molecule, LEC or to a linker if used. Reducing the immunogenicity of the invention cancer therapeutic agents can be addressed by methods well known in the art such as by attaching long chain polyethylene glycol (PEG)-based spacers, and the like, to the cancer targeting molecule, LEC or to a linker is used. Long chain PEG and other polymers are known for their ability to mask foreign epitopes, resulting in the reduced immunogenicity of therapeutic proteins that display foreign epitopes (Katre et al., *J. Immunol.* (1990,) 144, 209-213; Francis et al., *Int. J. Hematol.* (1998) 68, 1-18). Alternatively, or in addition, the individual administered the antibody-targeting molecule conjugate may be administered an immunosuppressent such as cyclosporin A, anti-CD3 antibody, and the like.

The following examples serve to illustrate the present invention. These examples are in no way intended to limit the scope of the invention.

EXAMPLES

Example 1

TNT Antibodies as Targeting Vehicles a. Chimeric TNT-3.

TNT monoclonal antibodies (MAbs) have been used to target solid tumors via degenerating cells located in necrotic regions of tumors (1). This approach can be used to target cancers of diverse origin while avoiding the problems of antigenic modulation and shedding. Three chimeric TNT MAbs were developed, chTNT-1, chTNT-2 and chTNT-3, target intranuclear antigens consisting of histone DNA complexes, heterochromatic DNA, and single-stranded DNA, respectively (4,5, Khawli, et al., *Cancer Biotherapy & Radiopharmaceuticals* (2002) 17: 359-370). The pharmacokinetic and biodistribution characteristics of each TNT MAb in tumor-bearing mice are presented. All three chimeric TNT MAbs were produced as previously described (Id.).

Six-week-old female BALB/c mice were used to determine the pharmacokinetic clearance of the chimeric TNT MAbs. Groups of mice (n=5) were administered i.p. injections of $^{125}$I-labeled MAb (30-40 µCi/mouse). chTNT-2 showed the longest circulation time ($T_{1/2}$=178.7 hours) compared to chTNT-1 ($T_{1/2}$=30.4 hours) and chTNT-3 ($T_{1/2}$=134.2 hours). Affinity binding studies were also conducted in which $^{125}$I labeled chimeric TNT MAbs were incubated with fixed Raji cells and the bound radioactivity used to calculate the affinity constant Ka by Schatchard analysis. The affinity constants of chTNT-1, -2, and -3 were $2.5 \times 10^9$ M$^{-1}$, $1.2 \times 10^9$ M$^{-1}$, and $1.4 \times 10^9$ M$^{-1}$, respectively.

To examine the tissue biodistribution of these MAbs, the MAD109 murine lung adenocarcinoma tumor model was used. The tumors were grown subcutaneously in the left flank for 5-7 days at which time they reached approximately 1 cm in diameter. Within each group, individual mice were injected i.v. with a 0.1 ml inoculum containing 100 µCi/10 µg of $^{125}$I-labeled MAb. As shown in Table 1, chTNT-1, -2, and -3 had different biodistribution characteristics in vivo and showed good uptake in this tumor model. For chTNT-2 and chTNT-3, the % injected dose/g tended to be higher than that for chTNT-1 in all organs. However, tumor-to-blood ratios for chTNT-1 were significantly higher (except for muscle and intestine) compared with those of chTNT-2 and chTNT-3. These results demonstrate the in vivo binding characteristics of each chimeric TNT MAb in tumor-bearing mice.

TABLE 1

One-Day Tissue Biodistribution of $^{125}$I-labeled chTNT-1, -2 and -3 MAbs in MAD109 Tumor-Bearing Mice.[a]

% Injected Dose/Gram (% ID/g)

| Organs  | chTNT-1      | chTNT-2      | chTNT-3      |
|---------|--------------|--------------|--------------|
| Blood   | 5.91((0.40)  | 11.8 (1.74)  | 10.2 (1.03)  |
| Lung    | 1.10 (0.07)  | 4.73 (0.18)  | 2.51 (0.47)  |
| Liver   | 0.85 (0.02)  | 4.81 (0.23)  | 2.91 (0.90)  |
| Spleen  | 0.79 (0.01)  | 3.60 (0.49)  | 4.48 (0.98)  |
| Stomach | 0.48 (0.04)  | 1.80 (0.23)  | 1.66 (0.36)  |
| Kidney  | 0.87 (0.02)  | 2.86 (0.43)  | 1.64 (0.28)  |
| Tumor   | 2.78 (0.20)  | 6.29 (0.62)  | 4.53 (0.88)  |

[a]Data are expressed as mean (Standard Deviation), n = 5 animals per group.

An imaging study was performed to demonstrate the ability of $^{131}$I-labeled chTNT-3 to localize to MAD109 tumor-bearing BALB/c mice. Imaging at day 1 and 3 showed strong signal at the tumor site indicating that chTNT-3 is able to localize and be retained within the tumor.

b. Characterization of a Phage Display Derived Human TNT-1 MAb NHS76.

Chimeric TNT-1 was first developed from the parent murine antibody by genetically engineering the murine variable regions to the human IgG$_1$ and kappa constant regions. Although the chimeric antibody's behavior was similar to that of the murine version, the 35% murine homology it shares allows for the potential of a human anti-mouse antibody (HAMA) response. To circumvent this problem, a fully human TNT-1 MAb, NHS76, was developed which showed similar binding characteristics to its murine counterpart. NHS76 was developed in collaboration with Cambridge Antibody Technologies (Cambridge, England) and was derived by screening a large scFv library using Raji Burkitt's lymphoma cell nuclear extracts (Sharifi, et al., *Hybridoma and Hybridomics*, (2001) 20: 305-312). It was expressed in the NS0 mouse myeloma cell line using the Glutamine Synthetase Expression System obtained from Lonza Biologicals, Inc. (Slough, England).

In order to demonstrate that this genetically engineered human counterpart to chTNT-1 had similar pharmacokinetic characteristics, in vivo behavior, and targeting abilities, both antibodies were rigorously tested in parallel. For these studies, biodistribution analysis in LS174T human colon tumor-bearing nude mice was performed to compare the uptake levels in tumor and normal organs. In addition, mouse imaging (FIG. 2) and autoradiographic (FIG. 3) studies were conducted to demonstrate positive uptake in necrotic regions of tumor and negative uptake in viable tissues and organs. For these studies, biodistribution was performed on days 1, 2, 3, 5, and 7 after i.v. injection of 125I-labeled MAbs. The tissue biodistribution for 1 to 7 days as depicted by the percent injected dose per gram of tissue and the tumor to normal organ ratios showed slower body clearance of the NHS76. As the blood levels drop, however, the amount of antibody remaining at the tumor normalizes to about 3% injected dose per gram by 7 days. This is comparable with the 3-day tumor retention level for chTNT-1. Also, phosphor screen autoradiography showed that NHS76 targeted to necrotic regions the LS174T tumor, while normal tissues were are seen to be relatively spared. The results of these studies confirmed the comparable nature of both humanized and chimeric TNT antibodies and provides pre-clinical data to demonstrate the suitability of NHS76 for use in humans.

Example 2

Cytokine Fusion Proteins

The production of several fusion proteins consisting of chTNT-3 and human IL-2 (Ref. no. 12), murine IFNγ (Ref. no. 9), human IFNγ and TNFα (Ref. no. 10), and muGM-CSF genetically linked to the C-terminal portion of chTNT-3 has been described. Their construction, testing, and use in immunotherapy experiments with the constructs are briefly described below.

a. Construction, Expression, and Purification of chTNT-3/Cytokine Fusion Proteins.

chTNT-3 (IgG1γ) was constructed and expressed as described previously (Ref. no. 5). Plasmids carrying the light and heavy chain genes of NHS76 (IgG$_1$κ) were produced as described previously (Ref. no. 10). The candidate scFv antibodies were converted to whole antibody using standard molecule biological techniques including restriction digestion, ligation, and polymerase chain reaction (PCR).

Figure 9:
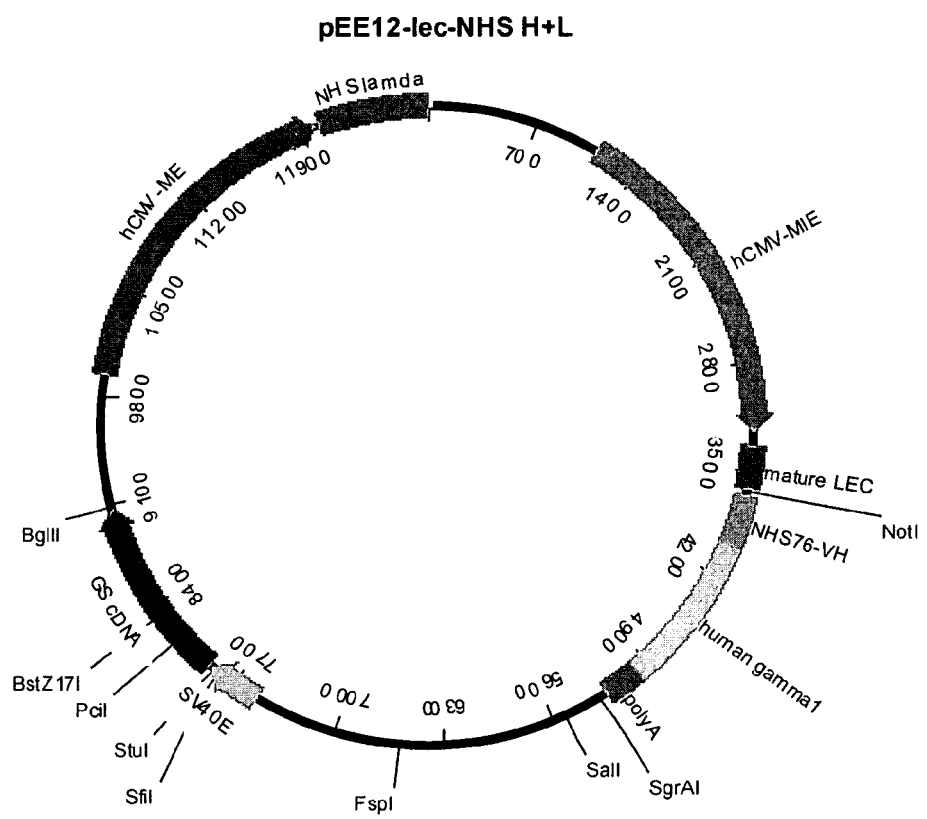
FIG. 9. Expression vector map for expressing LEC gene fused to NHS76. A linker consisting of Gly4Ser (SEO ID NO: 6) was inserted between the LEC gene and the NHS76 heavy chain variable region.

The human chemokine LEC gene was cloned by RT-PCR from the HepG2 hepatocarcinoma cell line. The mature cDNA of LEC was then amplified by PCR and inserted into the N-terminus of NHS76 heavy chain gene under the translation of an antibody leader sequence. The resulting fusion gene was then inserted into the expression vector pEE12, followed by insertion of the light chain (FIG. 9). The construct was electroporated into NS0 cells by the Glutamine Synthetase Gene Amplification System. The best expressing clone was chosen by an indirect ELISA assay of culture supernatant using crude DNA as antigen.

PCR fragments containing either the human IL-2, IFNγ, or TNFα cDNA preceded by a 7 amino acid linker peptide was inserted into the NotI site previously appended immediately downstream of the human γ1 terminal codon, producing a TNT-3 VH/human γ1/human cytokine fusion gene (Ref. no. 9, 10, 12). This resulted in the expression vectors pEE12/chTNT-3 HC/hIL-2, pEE12/chTNT-3 HC/muIFNγ, pEE12/chTNT-3 HC/TNFα, encoding a fusion protein consisting of the chimeric TNT-3 heavy chain with human IL-2, murine IFNγ, or TNFα at its C-terminus. These expression vectors were co-transfected with the expression vector for the chimeric TNT-3 light chain, pEE6/chTNT-3 light chain. The fusion protein was expressed in NS0 murine myeloma cells using the Glutamine Synthetase Gene Amplification System and purified from 8 liter aerated stir tank medium by tandem protein-A affinity and ion-exchange chromatography.

The chimeric antibody fusion proteins were properly assembled as demonstrated by reducing SDS-PAGE. Two bands were resolved for chTNT-3/hIL-2 at approximately 25 and 70 kD, corresponding to the molecular weights of the immunoglobulin light chain and heavy chain plus cytokine, compared to chTNT-3, whose heavy chain exhibited an apparent molecular weight of approximately 55 kD. Similarly, two bands were resolved for chTNT-3/muIFNγ (some breakdown seen) and chTNT-3/TNFα at approximately 25 and 70 kD corresponding to the predicted weights of the immunoglobulin light chain and heavy chain-cytokine fusion protein. For the muTNT-3/muGM-CSF construct, the cDNA fragment of mature muGM-CSF was inserted into the SpeI and EcoR1 sites at the murine γ2 terminal codon of the pEE12 expression vector. PEE12/muTNT-3/muGM-CSF was then co-transfected with pEE6/muTNT-3 light chain and the fusion protein was expressed in NS0 murine myeloma cells as described above. SDS-PAGE demonstrated two bands with approximate molecular weights of 25 and 70 KD, which corresponded to the muTNT-3 light chain and heavy chain/cytokine muGM-CSF fusion, respectively.

b. Bioactivity of MAb/Cytokine Fusion Proteins.

The biological activity of each of the cytokine moieties of the four fusion proteins was determined by in vitro assays. IL-2 bioactivity was demonstrated by testing its ability to support the proliferation of IL-2-dependent CTLL-2 cells (Gillis, et al., *J. Immunol.* (1978) 120: 2027-2031). Different concentrations of chTNT-3/IL-2, chTNT-3, or recombinant human IL-2 standard were incubated with IL-2 starved $2 \times 10^4$ CTLL-2 cells for 20 hr in a humidified 37° C., 5% $CO_2$ incubator. The cells were pulsed with $^3$H-thymidine for 6 hr, and the cell samples were harvested and counted. The activity of the chTNT-3/IL-2 was then determined by extrapolation or the rIL-2 curve in IU/mg.

For the muTNT-3/muGM-CSF fusion protein, the biological activity of the muGM-CSF moiety was determined by measuring its ability to support the proliferation of the cytokine dependent cell line FDC-P (Delta-Cruz, et al., *J. Immunol.* (2000) 165: 5112-5121). Briefly, 5,000 cells/well of FDC-P1 were pipeted into a 96-well culture plate in the presence of muGM-CSF or muTNT-3/muGM-CSF at a concentration range from 8 ng/ml to 4 pg/ml in triplicate. After 48 hr incubation in a humidified 37° C., 5% $CO_2$ incubator, cell proliferation was measured by a colorimetric method using the Promega Cell Proliferation Assay Kit (Madison, Wis.). From this assay, the ED50 for muTNT-3/muGM-CSF was shown to be 0.4-1.0 ng/ml.

For the muIFNγ moiety of the chTNT-3/muIFNγ fusion protein, an assay was performed to determine the induction of nitric oxide (NO) in RAW 264.7 murine macrophage cells (Kim, et al., *Journal of Immunological Methods*, (1996) 198:

203-209). Cells were grown in complete media supplemented with rmuIFN-γ, chTNT-3, or chTNT-3/muIFN-γ for 24 hr followed by analysis of the supernatant for nitrite ($NO_2$), a stable breakdown product of NO, using the Griess reagent. By this method, the specific activity of the chTNT-3/muIFN-γ fusion protein was calculated to be approximately 450 U/μg. chTNT-3 was negative in this assay. Biological Activity of chTNT-3/muIFN-γ was also measured by upregulation of MHC class II molecule expression in the WEHI-3 murine myelomonocytic cell line using flow cytometry. Cells were grown in complete media supplemented with recombinant muIFNγ, chTNT-3, or chTNT-3/muIFN-γ for 48 hr and then assayed for MHC class II molecule expression by flow cytometry. Using this method, the specific activity of the fusion protein was 430 U/μg (Ref. no. 9). In contrast, chTNT-3 was unable to induce MHC class II upregulation.

For the chTNT-3/huTNFα fusion protein, the biological activity of TNFα moiety was determined by the percent inhibition of Hep-2 cell growth as described previously (Hogan, M. M.: "Measurement of Tumor Necrosis Factor α and β" In: J. E. Colligan (ed.) Current Protocols in Immunology. New York: John Wiley & Sons, Inc. pp 6101-6105, 1993). Briefly, Hep-2 human epidermoid carcinoma cells were plated in 96 well culture plates at $1 \times 10^5$ cells/well in MEM with 10% FCS. The plates were incubated at 37° C. for 2-3 hours and the rhuTNFα or chTNT-3/TNFα was added to the plate in serial dilutions. To determine maximal lysis, 200 ng/ml of cycloheximide was used. Following the addition of the TNFα samples, the plates were again incubated at 37° C. for 18 hr, and then washed gently with PBS (200 μl/well). Cell death was quantified by a modified crystal violet assay. In this method, the chTNT-3/TNFα fusion protein was found to have a specific activity of 10.8 U/μg.

c. Immunoreactivity and Avidity Constants of the Fusion Proteins.

The immunoreactivity of the fusion proteins was determined by binding to fixed Raji lymphoma cells as described above. All the chTNT-3/cytokine fusion proteins were found to have similar binding constants ($0.5-1 \times 10^9$ $M^{-1}$) and were comparable to the binding constant of chTNT-3 ($1.4 \times 10^9 M^{-1}$) indicating that the genetic linkage of cytokines to the chTNT-3 heavy chain did not significantly interfere with antigen binding.

d. Pharmacokinetic and Biodistribution Studies.

Clearance and biodistribution studies were performed to determine pharmacokinetic clearance half-life and tumor uptake of all the fusion proteins. For pharmacokinetic studies, BALB/c mice were injected with $^{125}$I-labeled fusion protein or naked antibody, and the whole body activity at injection and selected times thereafter was measured with a microdosimeter. The results of these studies are shown in Table 2. Marked differences in clearance times are noted between the muIFNγ fusion protein and the IL-2, TNFα, and muGM-CSF fusion proteins. The chTNT-3 was found to have an unusually long half-life in these studies.

TABLE 2

Summary of Pharmacokinetic Clearance and Biodistribution Studies.

| Antibody or antibody/cytokine | Half-life (h) | Tumor Model | % Injected dose/gm of tumor at 3 days |
|---|---|---|---|
| chTNT-3 | 134 | MAD 109 | 13.5 |
| chTNT-3/muIFN-γ | 46 | MAD 109 | 2.4 |
| chTNT-3 | 134 | LS174T | 7.1 |
| chTNT-3/huIFN-γ | 19.1 | LS174T | 1.2 |
| chTNT-3/huIL-2 | 12 | LS174T | 1.7 |

TABLE 2-continued

Summary of Pharmacokinetic Clearance and Biodistribution Studies.

| Antibody or antibody/cytokine | Half-life (h) | Tumor Model | % Injected dose/gm of tumor at 3 days |
|---|---|---|---|
| chTNT-3/huTNF-α | 8 | LS174T | 1.3 |
| muTNT-3 | 150 | Colon 26 | 5.3 |
| muTNT-3/muGM-CSF | 15 | Colon 26 | 1.27 |

For the biodistribution studies, six-week old female BALB/c mice were inoculated subcutaneously in the left flank with approximately $10^7$ tumor cells. Five days later, when the tumors reached approximately 0.5-1 cm in diameter, the mice were injected intravenously with a 0.1 mL inoculum containing $^{125}$I-labeled antibody or $^{125}$I-labeled antibody/cytokine. Mice were sacrificed by sodium pentobarbital overdose 3 and/or 7 days post-injection and blood, tumor, and selected organs were removed and weighed as shown above. The results of these studies, summarized in Table 2, show that the pharmacokinetic effect of the rapid clearance of the fusion protein was evident when the tumor and normal organ biodistribution of chTNT-3 and chTNT-3/muIFN-γ are compared. For all the fusion proteins, tumor uptake was significantly lower than that seen for chTNT-3 at both 3 and 7 days post-injection. However the tumor to organ ratios, which reflect normal organ uptake and provide an indication of possible toxicity due to the cytokine, were either comparable or even slightly higher for all the fusion proteins.

In summary, the above in vitro characterization studies demonstrate that all the fusion proteins were able to maintain their binding affinity to antigen as well as their direct cytotoxic effect and immunomodulatory functions. In vivo, the fusion proteins were found to have a substantially shorter whole body half-life than parental chTNT-3, yet were able to target tumor as shown by biodistribution analysis. Due to their retention in tumor and rapid clearance from normal tissues, the fusion proteins were found to have equal or higher normal tissue/tumor ratios than chTNT-3.

Example 3

Chemokine Fusion Proteins a. Construction, Expression, and Purification of LEC/chTNT-3.

The plasmids carrying the light (pEE6/hCMV-LC) and heavy (pEE12/HC) chain genes of chTNT-3 (IgG$_1$κ) were produced as described previously (5,12). The human chemokine LEC gene was cloned by RT-PCR (Stephens, et al., *Eur. J. Immunol.* (2001) 31, 1247-1254) from the HepG2 hepatocarcinoma cell line using TRIzol (Invitrogen, Carlsbad, Calif.) to obtain total RNA. The mature cDNA of LEC was then amplified by PCR using primers 5'-TCTAGAAT-GAAGGTCTCCGAGGCTGCC-3' (SEQ ID NO: 4) and 5'-GCGGCCGCCTG-GGAGTTGAGGAGCTG-3' (SEQ ID NO: 5) inserted into the N-terminus of chTNT-3 heavy chain gene by Xba1 and Not1 under the translation of an antibody leader sequence. The resulting fusion gene was then inserted into the expression vector pEE12 and cotransfected with pEE6/TNT-3 light chain by electroporation into NS0 cells as prescribed by the Glutamine Synthetase Gene Amplification System. Cell culture medium was changed weekly after transfection for 3 weeks at which time the best expressing clone was chosen by an indirect ELISA assay of culture supernatant using crude DNA as antigen as previously described (5). To produce large quantities of the fusion protein, the high expressing clone was grown in aerated 8 liter stir flasks in selective media containing 5% heat-inactivated (68° C. for 1 hour with intermittent stirring), dialyzed fetal calf serum to eliminate the induction of proteolytic enzymes by the NS0 cells during incubation and the breakage of the fusion protein. The secreted fusion protein was then purified from clarified cell culture supernatant by tandem protein-A affinity and ion-exchange chromatography procedures. The purity of fusion protein was checked by SDS-PAGE electrophoresis under denaturing conditions and by HPLC using 0.05M phosphate buffer and 0.4M sodium perchlorate, pH 6.1 as the solvent system. After purification, the fusion protein was filtered through a 0.22 μm Nalgene disposable filter unit, aliquoted, and stored at −20° C. for long-term storage in 10 ml sterile tubes.

The C-terminus of the LEC gene was fused to the N-terminus of the chTNT-3 heavy chain gene using a 5 amino acid (Gly4Ser) linker (SEQ ID NO: 6). The fused LEC/chTNT-3 heavy chain gene (FIG. 1) was translated under an antibody leader and the expressed fusion protein was found to retain its biological activities as shown below. The highest LEC/chTNT-3 producing subclone secreted approximately 20 ug/ml/$10^6$ cells/24 hours in static culture. The molecular mass and assembly of the fusion protein was demonstrated by SDS-PAGE, which revealed two bands at approximately 67 and 25 kD, corresponding to the sum of the chimeric immunoglobulin heavy chain and LEC, and the antibody light chain, respectively. The purity of the construct was confirmed by HPLC, which showed that the LEC/chTNT-3 had a main peak with a retention time of approximately 442s. These analyses showed that the fusion protein remained intact even after storage at −20° C. for up to six months.

b. Chemotaxis Assay.

The bioactivity of the LEC fusion protein was demonstrated by measuring the migration of target cells in a 96-well microchemotaxis chamber (Neuroprobe, Gaithersburg, Md.) as described in the manufacturer's protocol. Briefly, LEC/chTNT-3, recombinant human LEC, or parental chTNT-3 were serially diluted from 0.39 nM to 50 nM in binding medium (RPMI 1640 with 1% BSA and 25 mmol/L HEPES) (Hedrick, et al., *Blood* (1998) 91:4242-4247; Zach-Howard, et al., *Blood* (2000) 96: 840-845). The solutions were placed in the lower chamber of the microchemotaxis apparatus. One hundred μL binding medium containing $10^5$ THP-1 human monocytic cells were then added to the upper chamber and after 1.5 hr of incubation in a humidified 5% $CO_2$, 37° C. incubator, the percentage of migrated cells was calculated to determine the migration index (average number of cells exposed to chemokine and fusion protein divided by the average number of cells exposed to binding media). All assays were performed in triplicate.

Free human recombinant LEC and the fusion protein induced THP-1 cell migration. The migration of THP-1 cells exposed to the fusion protein was dose dependent starting at a concentration as low as 1.6 nM and peaking at concentration of 12.5 nM. Free human recombinant LEC peaked at a higher concentration of about 25 nM in this assay. THP-1 cells exposed to the parental antibody (chTNT-3) did not show any migration verifying the biological activity of the LEC moiety of the fusion protein.

c. Radiolabeling of LEC/chTNT-3 and Stability of Radioconjugate.

$^{125}$I-labeled fusion protein was prepared using a modified chloramine-T method as described previously (5,7). Briefly, 1 mCi (37 MBq) of radioiodine and 20 μL of an aqueous solution of chloramine-T (2 mg/mL) were added to a 5 mL-test tube containing 100 μg LEC/chTNT-3 in 100 μL PBS. The solution was quenched after 2 min with 20 μL of an aqueous solution of sodium metabisulfite. Each reaction mixture was purified using a Sephadex G-25 column and typically recovered 90-95% yield. The radiolabeled antibodies were diluted with PBS for injection, stored at 4° C., and administered within 2 hr after radiolabeling. Radioiodinated antibodies were analyzed using an analytical instant thin layer chromatography (ITLC) system consisting of silica gel impregnated glass fiber (Gelman Sciences, Ann Arbor, Mich.). Strips (2×20 cm) were activated by heating at 110° C. for 15 min prior to use, spotted with 1 μL of sample, air dried, and eluted with methanol/H2O (80:20) for approximately 10 cm, again air dried, cut in half, and counted to determine protein bound and free radioiodine. ITLC analysis revealed an Rf value of 0 (MAb-bound) and a radiochemical purity of greater than 99%. In vitro serum stability was also evaluated as described previously (5). Briefly, radioiodinated MAbs were incubated for 48 h in mouse serum at 37° C. After trichloroacetic acid precipitation and centrifugation, MAb-bound radioactivity was measured in a gamma counter. Approximately 95% of the activity was trichloroacetic acid precipitable and virtually no release of free radioiodine was detected over this time period.

d. Avidity Determination.

In order to determine the avidity constant of the purified LEC/chTNT-3, a fixed cell radioimmunoassay was performed as described previously (12). Briefly, Raji lymphoma cells were washed once with PBS, fixed in EM grade 2% paraformaldehyde (Polysciences, Warrington, Pa.) for ten minutes at room temperature, and washed again in PBS before being stored in PBS containing 0.2% sodium azide at 4° C. Ten to 110 ng of $^{125}$I-labeled LEC/chTNT-3 was then incubated with $10^6$ fixed Raji cells for 1 hour at room temperature. The cells were washed 3× with PBS containing 1% BSA to remove any unbound antibody and counted in a gamma counter. The amount of fusion protein bound was determined from the remaining cell-bound radioactivity (cpm) and the specific activity of the fusion protein. Scatchard plot analysis of the data was used to obtain the slope from which the equilibrium or avidity constant K was calculated by the equation K=−(slope/n) where n is the valence of the antibody (2 for IgG). The LEC/chTNT-3 was found to have a similar binding constant ($1.0\times10^9$ M−1) to chTNT-3 ($1.4\times10^9 M^{-1}$) (5) indicating that the genetic linkage of LEC to the variable region of the chTNT-3 heavy chain did not significantly interfere with antigen binding.

e. Pharmacokinetic and Biodistribution Studies.

Six-week-old female BALB/c mice were used to determine the pharmacokinetic clearance of $^{125}$I-LEC/chTNT-3. A group of mice (n=5) previously fed with potassium iodide in the drinking water for 2-3 days to block the thyroid uptake of free radioiodide, were administered i.v. injections of $^{125}$I-labeled fusion proteins (30-40 μCi/mouse) using a 0.1 mL inoculum. The whole body activity at injection and selected time points post-injection was measured with a CRC-7 microdosimeter. The data were analyzed and half-lives were determined by the PSTRIP pharmacokinetic program (MicroMath, Inc., Salt Lake City, Utah). Results were expressed as the mean±standard deviation, and significance levels (P values) were determined using the Wilcoxon rank-sum test. From these studies, it was determined that the 125I-LEC/chTNT-3 was found to have a $T_{1/2}$ of 3 h±20 min (P≤0.01).

Groups of tumor-bearing BALB/c mice were used to determine the biodistribution of $^{125}$I-LEC/chTNT-3. Briefly, mice were injected with 0.2 ml containing $10^7$ MAD$10^9$ sc in the left flank using a University Animal Care Committee-approved protocol. The tumors were grown for 5 days until they reached approximately 0.5 cm in diameter. Mice were then injected i.v. with a 0.1 mL inoculum containing 100 µCi/10 µg of $^{125}$I-labeled LEC/chTNT-3. The mice were sacrificed by sodium pentobarbital overdose at 3, 6, 12, and 24 hr post-injection and organs, blood, and tumors were removed and weighed, and the radioactivity in the samples were measured in a gamma counter. For each mouse, the data were expressed as percent injected dose/gram (% ID/g) and tumor-to-organ ratio. $^{125}$I-LEC/chTNT-3 demonstrated a tumor uptake of 2.4% ID/g ($p \leq 0.01$) at both 12 and 24 hr post-injection. The rapid clearance of $^{125}$I-LEC/chTNT-3 also showed a decrease in radioactivity levels in blood and most of the other normal tissues ($p \leq 0.01$) at all time points resulting in high tumor-to-organ ratios. These data demonstrate that the radiolabeled LEC/chTNT-3 specifically bound to tumor with excellent retention at the tumor site.

Example 4

Immunotherapy Studies a. LEC/chTNT-3 Treatment.

Groups (n=7) of six-week old female BALB/c mice were injected subcutaneously in the left flank with a 0.2 mL inoculum containing approximately $10^7$ of MAD109 cells, Colon 26 cells, or RENCA cells under a University Animal Care Committee-approved protocol. The tumors were grown for 5-7 days until they reached approximately 0.5 cm in diameter. Groups of tumor-bearing mice were then treated intravenously with a 0.1 ml inoculum containing LEC/chTNT-3 (20 µg), PBS, or chTNT-3 (20 µg). All groups were treated daily×5 and tumor growth was monitored every other day by caliper measurement in three dimensions. Tumor volumes were calculated by the formula: length×width×height. The results were expressed as the mean±standard deviation and the significance levels (P values) were determined using the Wilcoxon rank-sum test.

Once tumors were established, mice were treated daily×5 with 20 µg of LEC/chTNT-3. As shown in FIG. 2 for two of the models, LEC/chTNT-3 treatment by day 19 of the study showed a 55% ($p \leq 0.05$) tumor growth reduction in the Colon 26 tumor model, a 37% ($p \leq 0.05$) reduction in the MAD109 tumor model, and a 42% ($p \leq 0.05$) reduction in the RENCA tumor model as compared to untreated controls.

b. Combination Therapy with Cytokine Fusion Proteins.

Figure 3:
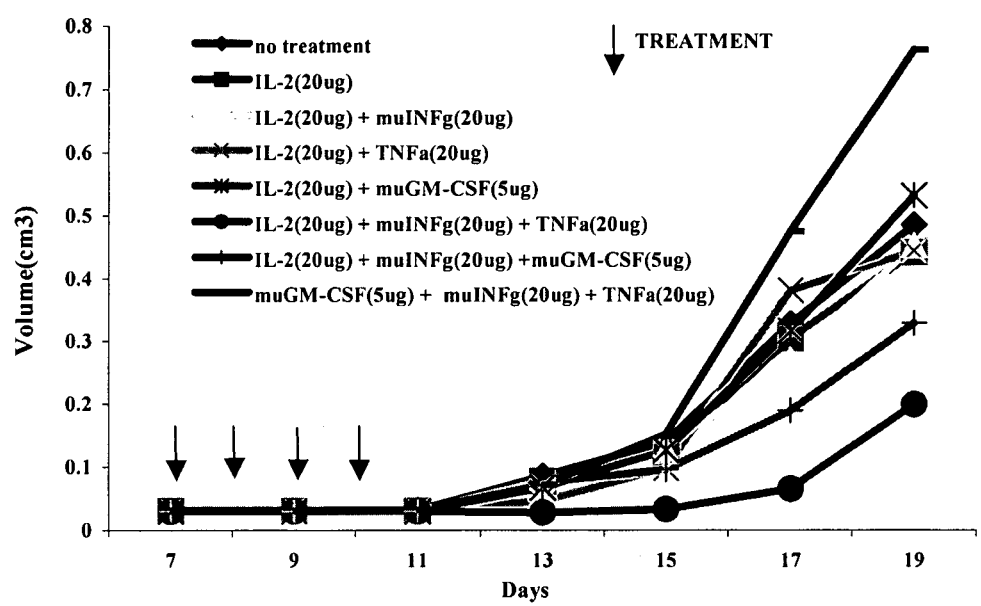
FIG. 3. Combination immunotherapy using chTNT-3/cytokine fusion proteins in RENCA renal carcinoma tumor model. Each fusion protein is abbreviated in the chart by listing the cytokine moiety.

The chTNT-3/cytokine fusion proteins were tested in different solid tumor models of the BALB/c mouse, including the COLON 26 colon adenocarcinoma, the MAD109 lung carcinoma, and as shown below in FIG. 3, the RENCA renal cell carcinoma. For these studies, 6-week old female BALB/C mice were injected subcutaneously with $5 \times 10^6$ tumor cells in the left flank. Five-seven days later when the tumors reached 0.5 cm in diameter (0.2 cm$^3$), the mice were divided into groups (n=5) and injected intravenously daily for four consecutive days. The growth of the tumors was then followed by caliper measurement every other day until day 17 when the experiments were terminated. The dose of the fusion proteins in a 0.1 ml inoculum was 20 µg except for chTNT-3/muGM-CSF which was more toxic necessitating the use of 5 µg/dose. When combinations of fusion proteins were used, they were premixed to keep the inoculum at 0.1 ml. Control groups received saline only or 20 µg of chTNT-3 which did not effect the growth curves of the three tumor models. A study of control groups from four individual experiment showed that the growth curves were very reproducible. The results of these experiments in the three tumor models shown in FIG. 3 demonstrated that, in two of these models, mice receiving the combination of chTNT-3/IL-2, chTNT-3/ TNFα, and chTNT-3/IFNγ exhibited the most tumor regression, estimated to be about 80% of control groups at day 17. Although individual fusion proteins had varying degrees of effectiveness in these tumor models, this combination or the one in which muTNT-3/muGM-CSF substituted for the chTNT-3/TNFα was most effective. Because a chimeric antibody was used in the construction of some of these fusion proteins, treatments were limited to one four-day course. Because of this limitation, the tumors began to grow at the same pace as those of the control groups soon after cessation of therapy. Hence, the therapeutic effects of these treatments were transient and the addition of a second or third course of treatment may be necessary to produce a more lasting effect and complete regression of tumor.

c. Combination Therapy with LEC/chTNT-3 with chTNT-3/Cytokine Fusion Proteins.

Figure 4:
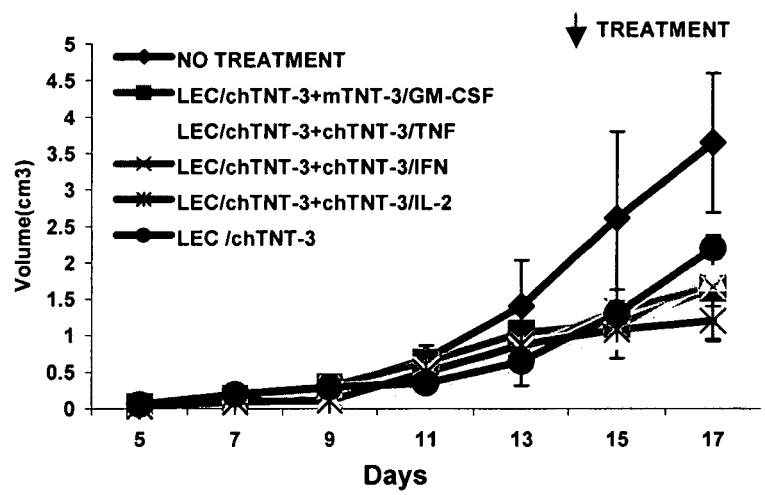
FIG. 4. Combination immunotherapy of LEC/chTNT-3 and chTNT-3/cytokine in MAD109-bearing BALB/c mice.

Six-week old female BALB/c mice were inoculated subcutaneously with approximately $5 \times 10^6$ MAD109 murine lung adenocarcinoma cells. Five days later when tumors reached 0.5 cm in diameter, the mice were injected with 0.1 ml of inoculum containing 20 µg of LEC/chTNT-3 alone or with 20 µg of chTNT-3/IFNγ, chTNT-3/TNFα, chTNT-3/GM-CSF or chTNT-3/IL-2. All groups were treated daily×5 and tumor growth was monitored every other day by caliper measurement in three dimensions. Tumor volumes were calculated by the formula: length×width×height. The results were expressed as the mean±standard deviation. As shown in FIG. 4, combination therapy with LEC/chTNT-3 and each of the four chTNT-3/cytokine fusion proteins produced only minimal improvement but the combination containing the chTNT-3/IL-2 did show flattening of the growth curve by day 17.

Example 5

Mechanism of Action Studies a. Immunohistochemical and Histological Studies of LEC/chTNT-3 Activity.

Groups of BALB/c mice were injected in the left flank with $10^7$ tumor cells as described above. Seven days after tumor implantation, mice were treated intravenously with LEC/chTNT-3 (20 µg), PBS, or chTNT-3 (20 µg) daily×5. Mice from each group were then sacrificed at 10, 12, 14 and 16 days after tumor implantation and tumors were excised and either fixed in 10% neutral buffered formalin (VWR Scientific, West Chester, Pa.) for paraffin embedding or snap frozen in liquid nitrogen in O.C.T. compound (Lab-Tek Products, Naperville, Ill.) for frozen sectioning. Paraffin embedded sections from MAD109 tumor-bearing mice were stained with hematoxylin and eosin (H&E) for morphological studies. For immunohistochemical studies, frozen sections of tumors from Colon 26 tumor-bearing mice were stained with biotinylated anti-CD4$^+$, anti-CD8$^+$, anti-CD11b$^+$, anti-Panendothelial, anti-CD11c$^+$, anti-CD19$^+$, anti-CD3e$^+$, and anti-45R$^+$ (BD PharMingen, San Diego, Calif.) antisera to stain lymphoid, PMN, and dendritic cell subpopulations. Sections were then incubated with HRP-conjugated streptavidin and developed with a colorimetric agent before being stained with hr & E. Microscopic findings were recorded using an Optronix digital camera.

The anti-cancer activity of chemokines has been attributed to the recruitment of dendritic cells, PMNs, and lymphoid cell subpopulations into the tumor and to their anti-angiogenic activity. Hence, it is of interest to identify which subpopulations were responsible for the anti-tumor activity of the LEC/chTNT-3. To accomplish this, histological and immunohistochemical studies were performed on tumor sections removed from treated mice. Surprisingly, morphological studies revealed that LEC/chTNT-3 treatment induced marked necrosis and congestion of blood vessels in the tumor samples studied.

The number of blood vessels in treated and control mice, however, was not found to be different as determined by immunohistochemical staining with a panendothelial antibody. LEC/chTNT-3 treated tumors also showed a marked infiltration of lymphoid cells in these sections. Immunohistochemical staining of tissue sections with B-cell, T-cell, dendritic cell, and PMNs specific antibodies was used to identify the presence of subpopulations infiltrating the tumors. For these studies, frozen sections from Colon 26-bearing BALB/c mice were prepared 4 days after the completion of treatment (16 days after tumor implantation) for immunohistochemical staining. The results of these studies revealed that the infiltration of PMNs, dendritic cells, B cells, and T cells was higher in the LEC/chTNT-3 treated tumors than the untreated group. Tumors removed at earlier time points showed that the infiltration of dendritic cells and macrophages were observed first by the third day of treatment and remained in the tumor until 4 days after the completion of treatment. By contrast, T-cell ($CD4^+$ and $CD8^+$) infiltration (15-20 cells/400× field) was less dramatic that that seen for dendritic cells and was first seen two days after the completion of therapy. Infiltration by PMNs and dendritic cells was perhaps the most dramatic findings in these studies.

b. Depletion Studies.

Figure 5:
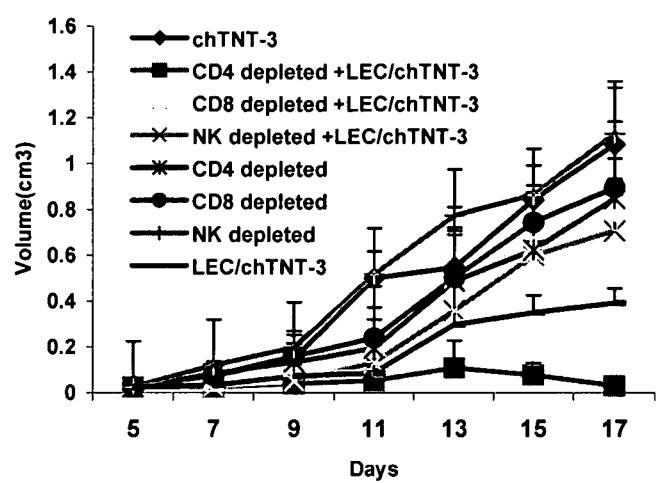
FIG. 5. T cell depletion studies with LEC/chTNT-3 showing combination therapy with anti-CD4+, CD8+, and NK cell antisera FIG. 6. T cell depletion studies with LEC/chTNT-3 showing anti-CD25+ antiserum.

In order to evaluate the subpopulation of T-cells that are responsible in part for the suppression of these tumor models, depletion studies were performed in conjunction with the above therapy studies. Groups of mice were transplanted with the Colon 26 colon carcinoma as above and when the tumors reached 0.5 cm in diameter, they received cytotoxic antisera specific for $CD4^+$ (0.5 mg/dose, clone GK1.5), $CD8^+$ (0.5 mg/dose, clone H35), or NK cells (0.35 mg/dose anti-asialo-GM) every 5 days which reduced each of these T-cell subpopulations to <2% in the peripheral circulation as shown by FACS analysis. If a particular subpopulation were to be instrumental for LEC/chTNT-3 immunotherapy, the observed tumor suppression induced by LEC/chTNT-3 would be prevented and the tumors would have a similar growth curve to control treated mice. As shown is FIG. 5, depletion by each of these antisera alone did not alter the growth of the tumors from that of the chTNT-3 treated control. By contrast, the LEC/chTNT-3 treated mice showed greater than 50% inhibition. As expected, $CD8^+$ and NK depletion therapy in combination with LEC/chTNT-3 treatment negated the anti-tumor activity of the LEC/chTNT-3 indicating that these lymphocyte subpopulations are very important in LEC function. By contrast, those mice which received $CD4^+$ depletion in combination with LEC/chTNT-3 therapy went to complete cure, an unexpected and potentially very significant finding.

Figure 6:
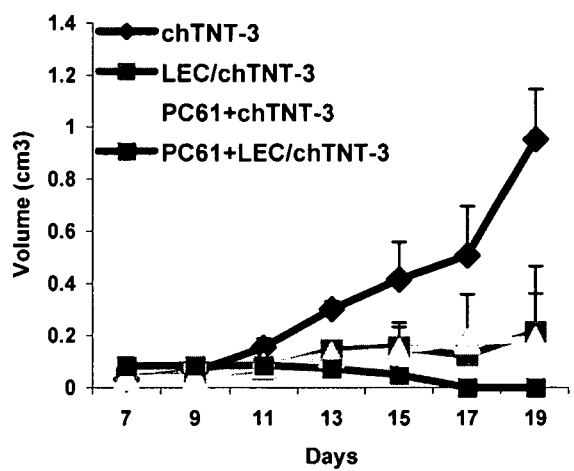

Additional depletion studies were next performed to determine if $CD4^+CD25^+$ T-cells which represent approximately 10% of the $CD4^+$ population could produce equally as impressive results when used in combination with LEC/chTNT-3. As shown below in FIG. 6, depletion of these T-cells using rat monoclonal antibody PC61 prior to the use of LEC/chTNT-3 was highly immunosuppressive to Colon 26 tumor growth in BALB/c mice demonstrating that this small population of T-immunoregulatory cells is responsible for suppression of the immune response during immunotherapy. It should be noted that in all these experiments, LEC/chTNT-3 immunotherapy was found to be entirely non-toxic in marked contrast to the use of chTNT-3/IL-2, chTNT-3/TNFα, and muTNT-3/muGM-CSF which demonstrated some form of toxicity in these experiments. Surprisingly, when PC61 was used to deplete $CD4^+CD25^+$ T-cells in combination with control chTNT-3, the Colon 26 tumors showed impressive reduction in tumor growth about as much as LEC/chTNT-3 alone. Both of these treatment groups, however, did not cure the mice of their implanted tumors. Complete and lasting remissions were not obtained until $CD4^+CD25^+$ T-cell depletion was performed in combination with LEC/chTNT-3.

REFERENCE LIST

1. Epstein, A. L., Chen, F-M., and Taylor, C. R.: A novel method for the detection of necrotic lesions in human cancers. *Cancer Res* 48:5842-5848, 1988.
2. Chen, F-M, Hansen, E. B., Taylor, C. R., and Epstein A. L.: Diffusion and binding of monoclonal antibody TNT-1 in multicellular tumor spheroids. *J. Natl. Cancer Inst.*, 83:200-204, 1991.
3. Epstein, A. L., Chen, D., Ansari, A., Najafi, A., Siegel, M., Lee, K., Hu, E., Rosen, P., Watkins, K., Stain, S., Weaver, F., and Taylor, C. R.: Radioimmunodetection of necrotic lesions in human tumors using I-131 labeled TNT-1 F(ab')$_2$ monoclonal antibody, *Antibody, Immunoconj, & Radiopharm*, 4:151-161, 1991.
4. Miller, G. K., Naeve, G. S., Gaffar, S. A., and Epstein, A. L.: Immunologic and biochemical analysis of TNT-1 and TNT-2 monoclonal antibody binding to histones. *Hybridoma* 12:689-698, 1993.
5. Hornick, J. L., Hu, P., Khawli, L. A., Biola, B. H., Yun, A., Sharifi, J., Taylor, C. R., and Epstein, A. L.: chTNT-3/B, a new chemically modified chimeric monoclonal antibody directed against DNA for the tumor necrosis treatment of solid tumors. *Cancer Biother and Radiopharm* 13:255-268, 1998.
6. Giovarelli M, Cappello P, Forni G, Salcedo T M, Paul A., LeFleur D W, Nardelli B, Carlo E D, Lollini P-L, Ruben S, Ullrich S, Garotta G, Musiani P. Tumor rejection and immune memory elicited by locally released LEC chemokine are associated with and impressive recruiteent of APCs, lymphocytes, and granulocytes. *J Immunol.* 164:3200-3206, 2000.
7. Sharifi, J., Khawli, L. A., Hu, P., King, S. and Epstein, A. L.: Characterization of a Phage Display-Derived Human Monoclonal Antibody (NHS76) Counterpart to Chimeric TNT-1 Directed Against Necrotic Regions of Solid Tumors. *Hybridoma and Hybridomics,* 20: 305-312, 2001.
8. Chen, F-M., Epstein, A. L., Li, Z., and Taylor, C. R.: A comparative autoradiographic study demonstrating differential intra-tumor localization of monoclonal antibodies to cell surface (Lym-1) and intracellular (TNT-1) antigens. *J. Nucl. Med.,* 31:1059-1066, 1990.
9. Mizokami, M. M., Hu, P., Khawli, L. A. and Epstein, A. L.: Chimeric TNT-3 antibody-murine-interferon-γ fusion protein for the immunotherapy of solid malignancies. Submitted.
10. Sharifi, J. Khawli, L. A., Hu, P., Epstein, A. L.: Generation of human interferon gamma and tumor necrosis alpha chimeric TNT-3 fusion proteins. *Hybridoma and Hybridomics,* 21: 421-432, 2002.
11. Hornick, J. L., Khawli, L. A., Hu, P., Lynch, M., Anderson, P. M., and Epstein, A. L.: Chimeric CLL-1 antibody fusion proteins containing granulocyte-macrophage colony-stimulating factor or interleukin-2 with specificity for B-cell malignancies exhibit enhanced effector functions while retaining tumor targeting properties. *Blood* 89:4437-4447, 1997.

12. Hornick, J. L., Khawli, L. A., Hu, P., Khanna, C., and Epstein, A. L: A monoclonal antibody/Interleukin-2 fusion protein directed against DNA enhances the delivery of therapeutic molecules to solid tumors. *Clin Cancer Res* 5:51-60, 1999.

13. LeBerthon, B., Khawli, L. A., Miller, G. K., Charak, B. S., Amitabha, M. and Epstein. A. L.: Enhanced tumor uptake of macromolecules induced by a novel vasoactive Interleukin-2 immunoconjugate. *Cancer Res.,* 51: 2694-2698, 1991.

14. Khawli, L. A., Miller, G. K. and Epstein, A. L.: Effect of seven new vasoactive immunoconjugates on the enhancement of monoclonal antibody uptake in tumors. *Cancer* (Supplement to), 73(3): 824-831, 1994.

15. Khawli, L. A., Hornick, J. L., Sharifi, J. and Epstein, A. L.: Improving the chemotherapeutic index of IUdR using a vasoactive immunoconjugate. *Radiochimica Acta,* 79: 83-86, 1997.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Other embodiments are set forth within the following claims.

What is claimed is:

1. A cancer therapeutic agent, comprising an antibody, wherein said antibody is a murine, chimeric, humanized, or human form of murine antibody TNT-1, TNT-2, TNT-3 or NHS76, linked to a liver-expressed chemokine (LEC), wherein said LEC comprises an amino acid sequence which has at least 95% sequence identity with SEQ ID NO: 3 and acts as a chemotactic factor for one or more of macrophages, monocytes, dendritic cells, T cells, PMNs and lymphoid cells or the production of IFN-(gamma) or IL-12, and wherein said agent is a fusion protein and wherein the C-terminus of said LEC is fused to the N-terminus of said antibody.

2. The cancer therapeutic agent according to claim 1, wherein said antibody is specific for an intracellular antigen.

3. The cancer therapeutic agent according to claim 2, wherein said antibody is specific for an intranuclear antigen.

4. The cancer therapeutic agent according to claim 1 wherein said antibody is NHS76.

5. The cancer therapeutic agent according to claim 1, wherein said LEC comprises an amino acid sequence which has at least 98% sequence identity with SEQ ID NO: 3.

6. The cancer therapeutic agent according to claim 1, wherein said LEC comprises the amino acid sequence shown in SEQ ID NO: 3.

7. A composition, comprising the cancer therapeutic agent of claim 1 and a pharmaceutically acceptable carrier.

* * * * *